United States Patent [19]
Wetzel et al.

[11] 4,016,263
[45] Apr. 5, 1977

[54] N-SUBSTITUTED ERYTHROMCYLAMINES AND SALTS THEREOF

[75] Inventors: Bernd Wetzel; Eberhard Woitun; Roland Maier, all of Biberach; Wolfgang Reuter, Laupertshausen; Hanns Goeth, Biberach; Uwe Lechner, Ummendorf, all of Germany

[73] Assignee: Boehringer Ingelheim GmbH, Ingelheim am Rhine, Germany

[22] Filed: Mar. 29, 1976

[21] Appl. No.: 671,422

[30] Foreign Application Priority Data

Apr. 7, 1975 Germany ................... 2515078
Feb. 19, 1976 Germany ................... 2606663
Feb. 19, 1976 Germany ................... 2606662

[52] U.S. Cl. .................................. 424/180; 536/9
[51] Int. Cl.$^2$ ........................................ A61K 31/70
[58] Field of Search ............... 536/9; 424/180; 671/421

[56] References Cited
UNITED STATES PATENTS 3,939,144 2/1976 Radobolja ..................... 236/9

*Primary Examiner*—Lewis Gotts
*Assistant Examiner*—Cary Owens
*Attorney, Agent, or Firm*—Hammond & Littell

[57] ABSTRACT

Compounds of the formula

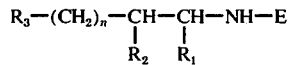

wherein E is

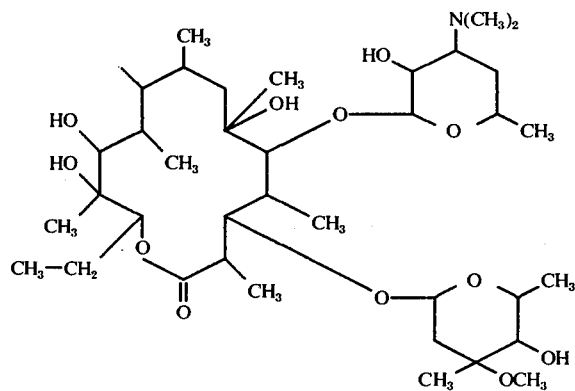

$R_1$ is hydrogen; straight or branched alkyl of 1 to 3 carbon atoms; (alkoxy of 1 to 5 carbon atoms)-(alkyl of 1 to 3 carbon atoms); phenyl; or benzyl;

$R_2$ is hydrogen; hydroxyl; straight or branched alkyl of 1 to 3 carbon atoms; or phenyl;

$R_3$ is hydroxyl; alkanoyloxy of 1 to 5 carbon atoms; benzoyloxy; straight or branched alkoxy of 1 to 5 carbon atoms; amino; mono(alkyl of 1 to 5 carbon atoms)-amino; dialkyl-amino, where the sum of carbon atoms in the alkyls is from 2 to 8, inclusive; mono(hydroxy-alkyl of 1 to 4 carbon atoms)-amino; di(hydroxy-alkyl)-amino, where the sum of carbon atoms in the alkyls is from 2 to 8, inclusive; phenyl(alkyl of 1 to 2 carbon atoms)-amino; phenyl-amino, where the phenyl moiety may optionally have one or more halogen, alkyl of 1 to 3 carbon atoms, alkoxy of 1 to 3 carbon atoms or hydroxyl substituents attached thereto; (alkanoyl of 1 to 5 carbon atoms)-amino; phenyl(alkanoyl of 1 to 5 carbon atoms)-amino; benzoyl-amino; methoxybenzoyl-amino; halobenzoyl-amino; carboxybenzoyl-amino; p-tolylsulfonamino; -HN-NR$_4$R$_5$, where R$_4$ and R$_5$ are alkyl of 1 to 3 carbon atoms or, together with each other and the nitrogen atom to which they are attached, form a 5- to 6-membered heterocycle optionally comprising an additional oxygen, sulfur or nitrogen heteroatom in the ring, and said additional nitrogen heteroatom optionally having an alkyl of 1 to 5 carbon atoms substituent attached thereto;

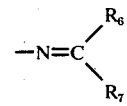

where $R_6$ is amino; mono(straight or branched alkyl of 1 to 8 carbon atoms)-amino; dialkylamino, where the sum of carbon atoms in the alkyls is from 2 to 6, inclusive; cyclohexyl-amino; N-(alkyl of 1 to 3 carbon atoms)-N-cyclohexyl-amino; dicyclohexyl-amino; methoxy(alkyl of 1 to 3 carbon atoms)-amino; di-methoxy(alkyl of 1 to 3 carbon atoms)-amino; benzyl-amino, where the phenyl moiety may optionally have from one to three (alkoxy of 1 to 3 carbon atoms)-substituents attached thereto; phenethyl-amino, where the phenyl moiety may optionally have from one to three(alkoxy of 1 to 3 carbon atoms)-substituents attached thereto; dibenzyl-amino; di(phenethyl)-amino; benzhydrylamino; N-methyl-N-benzyl-amino; N-phenyl-N-benzyl-amino; N-methyl-N-phenylamino; N-ethyl-N-phenyl-amino; piperidino; methyl-piperidino; benzyl-piperidino; pyrrolidino; methyl-pyrrolidino; benzyl-pyrrolidino; morpholino; methyl-morpholino; benzyl-morpholino; piperazino; methyl-piperazino; benzyl-piperazino; hexamethyleneimino; methyl-hexamethyleneimino; benzyl-hexamethyleneimino; thiomorpholino; methyl-thiomorpholino; benzyl-thiomorpholino; heptamethyleneimino; methyl-heptamethyleneimino; or benzyl-heptamethylimino; and $R_7$ is amino; cyclohexylamino; di(alkyl of 1 to 3 carbon atoms)-amino; benzyl-amino; phenethylamino; dibenzyl-amino; phenoxy-methyl-amino; phenoxyethyl-amino; N-phenyl-N-benzyl-amino; N-methyl-N-phenyl-amino; piperidino, benzyl-piperidino; pyrrolidino; benzyl-pyrrolidino; morpholino; benzyl-morpholino; piperazino; benzyl-piperazino; thiomorpholino; benzyl-thiomorpholino; hexamethyleneimino; benzyl-hexamethyleneimino; hydrogen; alkyl of 1 to 3 carbon atoms; cyclohexyl, benzyl, methoxy-benzyl; phenethyl; methoxyphenethyl; thienyl; furyl; pyridyl; (alkyl of 1 to 3 carbon atoms)-thio; methoxy(alkyl of 1 to 3 carbon atoms)-thio; cyano(alkyl of 1 to 3 carbon atoms)-thio; benzyl-thio; methylbenzyl-thio; phenyl-thio; or tolyl-thio;

$R_3$ = is also NH-A-B, where A is alkylene of 1 to 4 carbon atoms; and B is alkoxy of 1 to 3 carbon atoms, di(alkyl of 1 to 3 carbon atoms)-amino or carbalkoxy of 2 to 4 carbon atoms;

thiazolyl-amino; or pyridyl-amino; and n is 0 or 1;

and non-toxic, pharmacologically acceptable acid addition salts thereof. The compounds as well as their salts are useful as antibacterials.

13 Claims, No Drawings

N-SUBSTITUTED ERYTHROMCYLAMINES AND SALTS THEREOF

This invention relates to novel N-substituted erythromycylamines and non-toxic acid addition salts thereof, as well as to various methods of preparing these compounds.

More particularly, the present invention relates to a novel class of erythromycylamine derivatives represented by the formula

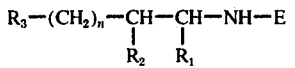

wherein E is

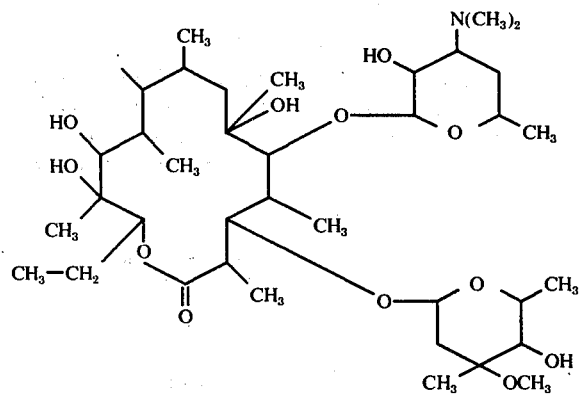

$R_1$ is hydrogen; straight or branched alkyl of 1 to 3 carbon atoms; (akoxy of 1 to 5 carbon atoms)-(alkyl of 1 to 3 carbon atoms); phenyl; or benzyl;

$R_2$ is hydrogen; hydroxyl; straight or branched alkyl of 1 to 3 carbon atoms; or phenyl;

$R_3$ is hydroxyl;
alkanoyloxy of 1 to 5 carbon atoms;
benzoyloxy;
straight or branched alkoxy of 1 to 5 carbon atoms;
amino;
mono(alkyl of 1 to 5 carbon atoms)-amino;
dialkyl-amino, where the sum of carbon atoms in the alkyls is from 2 to 8, inclusive;
mono(hydroxy-alkyl of 1 to 4 carbon atoms)-amino;
di(hydroxy-alkyl)-amino, where the sum of carbon atoms in the alkyls is from 2 to 8, inclusive;
phenyl(alkyl of 1 to 2 carbon atoms)-amino;
phenyl-amino, where the phenyl moiety may optionally have one or more halogen, alkyl of 1 to 3 carbon atoms, alkoxy of 1 to 3 carbon atoms or hydroxyl substituents attached thereto;
(alkanoyl of 1 to 5 carbon atoms)-amino;
phenyl(alkanoyl of 1 to 5 carbon atoms)-amino;
benzoyl-amino;
methoxybenzoyl-amino;
halobenzoyl-amino;
carboxybenzoyl-amino;
p-tolysulfonamino;
-HN-NR$_4$R$_5$, where R$_4$ and R$_5$ are alkyl of 1 to 3 carbon atoms or, together with each other and the nitrogen atom to which they are attached, form a 5- to 6-membered heterocycle optionally comprising an additional oxygen, sulfur or nitrogen heteroatom in the ring, and said additional nitrogen heteroatom optionally having an alkyl of 1 to 5 carbon atoms substituent attached thereto;

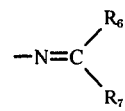

where
$R_6$ is amino; mono(straight or branched alkyl of 1 to 8 carbon atoms)-amino; dialkylamino, where the sum of carbon atoms in the alkyls is from 2 to 6, inclusive; cyclohexyl-amino; N-(alkyl of 1 to 3 carbon atoms)-N-cyclohexyl-amino; dicyclohexyl-amino; methoxy-(alkyl of 1 to 3 carbon atoms)-amino; di-methoxy(alkyl of 1 to 3 carbon atoms)-amino; benzyl-amino, where the phenyl moiety may optionally have from one to three (alkoxy of 1 to 3 carbon atoms)-substituents attached thereto; phenethyl-amino, where the phenyl moiety may optionally have from one to three (alkoxy of 1 to 3 carbon atoms)-substituents attached thereto; dibenzyl-amino; di(phenyl)-amino; benzhydryl-amino; N-methyl-N-benzyl-amino; N-phenyl-N-benzyl-amino; N-methyl-N-phenyl-amino; N-ethyl-N-phenyl-amino; piperidino; methy-piperidino; benzyl-piperidino; pyrrolidino; methyl-pyrrolidino; benzyl-pyrrolidino; morpholino; methyl-morpholino; benzyl-morpholino; piperazino; methyl-piperazino; benzyl-piperazino; hexamethyleneimino; methyl-hexamethyleneimino; benzyl-hexamethyleneimino; thiomorpholino; methyl-thiomorpholino; benzyl-thiomorpholino; heptamethyleneimino; methyl-heptamethyleneimino; or benzyl-heptamethyleneimino; and $R_7$ is amino; cyclohexylamino; di(alkyl of 1 to 3 carbon atoms)-amino; benzyl-amino; phenethyl-amino; dibenzyl-amino; phenoxy-methyl-amins; phenoxyethyl-amino; H-phenyl-N-benzyl-amino; N-methyl-N-phenyl-amino; piperidino; benzyl -piperidino; pyrrolidino; benzyl-pyrrolidino; morpholino; benzyl-morpholino; piperazino; benzyl-piperazino; thiomorpholino; benzyl-thiomorpholine; hexamethyleneimino; benzyl-hexamethyleneimino; hydrogen; alkyl of 1 to 3 carbon atoms; cyclohexyl; benzyl; methoxy-benzyl; phenethyl; methoxyphenethyl; thienyl; furyl; pyridyl; (alkyl of 1 to 3 carbon atoms)thio; methoxy(alkyl of 1 to 3 carbon atoms) -thio; cyano(alkyl of 1 to 3 carbon atoms) -thio; benzyl-thio; methylbenzyl-thio; phenyl-thio; or tolyl-thio;

$R_3 =$ is also
-NH-A-B, where A is alkylene of 1 to 4 carbon atoms; and B is alkoxy of 1 to 3 carbon atoms; di(alkyl of 1 to 3 carbon atoms)-amino or carbalkoxy of 2 to 4 carbon atoms;
thiazolyl-amino; or
pyridyl-amino; and
$n$ is 0 or 1;
and non-toxic, pharmacologically acceptable acid addition salts thereof.

The compounds embraced by formula I may be prepared by the following methods:

METHOD A

For the preparation of a compound of the formula I wherein $R_3$ has the above-defined meanings except

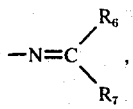

by reductive condensation of erythromycylamine of the formula $$H_2N\text{-}E \qquad (II)$$

wherein E has the meaning previously defined, with an aldehyde or ketone of the formula

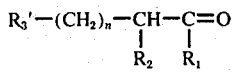

wherein $R_1$, $R_2$ and n have the same meanings as in formula I and $R_3'$ has the same meanings as $R_3$ in formula I except

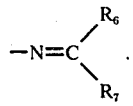

If $R_3'$ is free or monosubstituted amino, these groups must be protected by a protective group which can easily be split off, such as trityl, carbobenzoxy or 2-nitrophenylsulfenyl. During the reaction these protective groups are split off again.

An azomethine of the formula

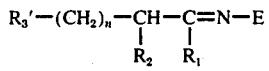

wherein $R_1$, $R_2$, $R_3'$, n and E have the meanings previously defined, and which is formed as an intermediate, may either be isolated first and subsequently reduced, or the reaction may also be carried out in situ without isolation of the azomethine intermediate.

The reaction is preferably carried out in a polar organic solvent, such as methanol, ethanol, dioxane, tetrahydrofuran, dimethylformamide or methylene chloride, at temperatures between −25° C and +100° C. However, the condensation may also be effected in the absence of a solvent.

Examples of suitable reducing agents are either hydrogen in the presence of a finely divided metal, such as palladium, platinum or Raney nickel, at pressures between 1 and 150 atmospheres; or a metal hydride, such as lithium borohydride, sodium borohydride, lithium cyanoborohydride or an alkali metal alkoxy aluminum hydride.

METHOD B

For the preparation of a compound of the formula I wherein $R_3$ is free amino, by catlytic reduction of an N-cyanoalkyl or N-nitroalkyl-erythromycylamine of the formula

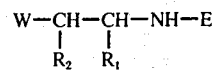

wherein $R_1$, $R_2$ and E have the meanings previously defined, and W is cyano or nitro; when W is cyano, a compound of the formula I wherein n is 1 is obtained; when W is nitro; a compound of the formula I wherein n is 0 is obtained.

The reduction is carried out with hydrogen in the presence of a finely divided metal, such as palladium, platinum, Raney nickel or Raney cobalt, in the presence of a solvent, such as water, methanol, ethanol, dioxane or tetrahydrofuran, at temperatures between 0° and 150° C and at a pressure between 1 and 150 atmospheres.

METHOD C

For the preparation of a compound of the formula I, wherein n is 0 and $R_3$ is hydroxyl, amino or monoalkylated amino, by alkylation of erythromycylamine (formula II) with an alkylene oxide or an alkylene imine of the formula

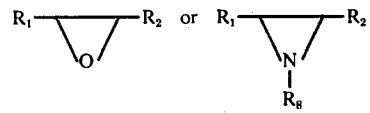

wherein $R_1$ and $R_2$ have the meanings previously defined, and $R_8$ is hydrogen or alkyl of 1 to 3 carbon atoms.

The reaction of erythromycylamine with a compound of the formula V yields a compound of the formula I wherein $R_3$ is hydroxyl, whereas the reaction with a compound of the formula VI yields a compound of the formula I wherein $R_3$ is amino or monoalkylated amino.

The alkylation is carried out in a solvent, such as an alkanol or a mixture of an alkanol and water, at a temperature between 0° C and the boiling point of the reaction mixture, preferably at a temperature between 0° and 100° C.

METHOD D

For the preparation of a compound of the formula I wherein n is 1 and $R_3$ is hydroxyl, by reduction of an azomethine aldehyde of the formula

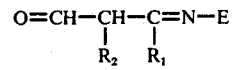

wherein $R_1$, $R_2$ and E have the meanings previously defined, with hydrogen in the presence of a finely divided metal, such as palladium, platinum, Raney nickel or Raney cobalt, and in the presence of a solvent, such as methanol, ethanol or dioxane, at a temperature between 0° and 150° C and a pressure between 1 and 150 atmospheres; or with a metal hydride, such as lithium borohydride, sodium borohydride, lithium cyanoborohydride or an alkali metal alkoxy aluminum hydride, at a temperture between −25° C and +50° C.

METHOD E

For the preparation of a compound of the formula I wherein n is 0 and $R_3$ is hydroxyl, by reduction of an azomethine-aldehyde or -ketone of the formula

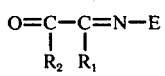

$$O=C-C=N-E \quad \text{(VIII)}$$
$$\phantom{O=C}|\phantom{-C}| $$
$$\phantom{O=C}R_2\phantom{-}R_1$$

wherein $R_1$, $R_2$ and E have the meanings previously defined, either with hydrogen in the presence of a finely divided metal, such as palladium, platinum, Raney nickel or Raney cobalt, in the presence of a solvent, such as methanol, ethanol or dioxane, at a temperature between 0° and 150° C and a pressure between 1 and 150 atmospheres; or with a metal hydride, such as lithium borohydride, sodium borohydride, lithium cyanoborohydride or an alkali metal alkoxy aluminum hydride, at a temperature between −25° C and +50° C.

METHOD F

For the preparation of a compound of the formula I wherein n is 0 and $R_3$ is amino, monoalkylamino of 1 to 5 carbon atoms, straight or branched hydroxyalkylamino of 1 to 4 carbon atoms, phenylalkylamino with 1 to 2 carbon atoms in the alkylene moiety, phenylamino, -hn-a-b as defined above, -HN-$NR_4R_5$ as defined above, by reduction of an azomethine of the formula

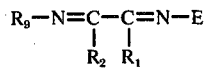

$$R_9-N=C-C=N-E \quad \text{(IX)}$$
$$\phantom{R_9-N=C}|\phantom{-C}|$$
$$\phantom{R_9-N=C}R_2\phantom{-}R_1$$

wherein $R_1$, $R_2$ and E have the meanings previously defined and $R_9$ is hydrogen, alkyl of 1 to 5 carbon atoms, straight or branched hydroxyalkyl of 1 to 4 carbon atoms, phenylalkyl with 1 to 2 carbon atoms in the alkylene moiety, phenyl, -A-B as defined above, thiazolyl, pyridyl or -$NR_4R_5$ as defined above, either with hydrogen in the presence of finely divided metal, such as palladium, platinum, Raney nickel or Raney cobalt, in the presence of a solvent, such as methanol, ethanol or dioxane, at a temperature between 0° and 150° C and a pressure between 1 and 150 atmospheres; or with a metal hydride, such as lithium borohydride, sodium borohydride, lithium cyanoborohydride or an alkali metal alkoxy aluminum hydride at a temperature between −25° C and +50° C.

METHOD G

For the preparation of a compound of the formula I wherein $R_3$ is a monoalkylamino, dialkylamino, straight or branched hydroxyalkylamino, straight or branched di(hydroxyalkyl)-amino, -HN-A-B as defined above, thiazolylamino, pyridylamino or phenylalkylamino, by reaction of an N-aminoalkyl-erythromycylamine of the formula

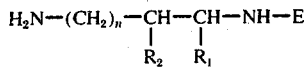

$$H_2N-(CH_2)_n-CH-CH-NH-E \quad \text{(X)}$$
$$\phantom{H_2N-(CH_2)_n-}|\phantom{-CH}|$$
$$\phantom{H_2N-(CH_2)_n-}R_2\phantom{-}R_1$$

wherein $R_1$, $R_2$, E and n have the meanings previously defined, with a carbonyl compound, such as formaldehyde, acetaldehyde, benzaldehyde, phenylacetaldehyde or an aliphatic hydroxyaldehyde, under reducing conditions, or with an alkylene oxide; in the last case a compound of the formula I wherein $R_3$ is straight or branched hydroxyalkylamino or di(hydroxyalkyl)amino is obtained.

The reductive condensation of a compound of the formula X with a carbonyl compound is preferably carried out in the presence of a polar organic solvent, such as methanol, ethanol, dioxane or tetrahydrofuran, at a temperature between −25° C and +100° C, using hydrogen in the presence of a finely divided metal, such as palladium, platinum, Raney nickel or Raney cobalt, at a pressure between 1 and 150 atmospheres; or a metal hydride, such as lithium borohydride, sodium borohydride, lithium cyanoborohydride or an alkali metal alkoxy aluminum hydride, as the reducing agent.

The alkylation of a compound of the formula X with an alkylene oxide is carried out in the presence of a solvent, such as an alkanol or alkanol-water mixture, at a temperature between 0° and 100° C.

If a compound of the formula X is reacted with the alkylating agent in the molar ratio of 1:1, a compound of the formula I is obtained, wherein $R_3$ is a secondary amino group; if the molar ratio is 1:2, a compound of the formula I is obtained, wherein $R_3$ is a tertiary amino group.

METHOD H

For the preparation of a compound of the formula I, wherein $R_3$ is optionally phenyl-substitured alkanoyl amino of 1 to 5 carbon atoms in the acyl moiety, benzamido or p-toluenesulfonamido, by reaction of an N-aminoalkyl-erythromycylamino of the formula X with a acylating agent, such as an acid halide, an acid anhydride, an acid amideacetal or an acid aminal ester of the corresponding aliphatic, araliphatic or aromatic carboxylic acid; the reaction with acid halides is optionally carried out in the presence of a hydrogen halide binding agent.

The reaction is carried out in an inert organic solvent at a temperature between −20° C and +50° C, preferably between −5° and +10° C. Suitable solvents are ethers, such as diethyl ether, dioxane, or tetrahydrofuran, methylene chloride or aromatic hydrocarbons.

METHOD I

For the preparation of a compound of the formula I wherein $R_3$ is guanidine ($R_6$ and $R_7 = -NH_2$), by reaction of an N-aminoalkyl-erthromycylamine of the formula X with a guanidination agent, such as a 1-guanyl-3,5-dimethylpyrazole, S-alkyl isothiourea or O-alkylisourea salt. The reaction is preferably carried out in the presence of a polar solvent, such as methanol, ethanol, dioxane, tetrahydrofuran or a mixture of any one of these solvents with water, at a temperaure between −25° and +100° C.

METHOD J

For the preparation of a compound of the formula I, wherein $R_3$ is substituted guanidino ($R_6$ and/or $R_7$ are substituted amino), substituted amidino ($R_6$ is substituted amino, and $R_7$ is hydrogen, alkyl, cyclohexyl, benzyl, phenylethyl, phenyl, thienyl, furyl or pyridyl), or substituted isothioureido ($R_6$ is substituted amino, $R_7$ is alkylthio, benzyl or phenylthio), by reaction of a N-aminoalkyl-erythromycylamine of the formula X with a halocarbamidinium salt, a carboxylic acid-imidium-halide salt or a halothiocarbonic acid-imidium-S-ester salt of the formula

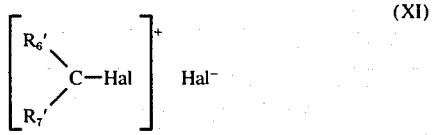

wherein $R_6'$ and $R_7'$ have the meanings given above for $R_6$ and $R_7$ except free amino, and Hal is halogen, in the presence of a hydrogen halide binding agent.

The reaction is carried out in the presence of an inert solvent, such as benzene, toluene, chlorobenzene, carbon tetrachloride, chloroform, methylene chloride or acetonitrile, under exclusion of moisture and at a temperature between −25° and +100° C. An equimolar quantity of a tertiary organic base, such as triethylamine, or an inorganic base, such as anhydrous sodium bicarbonate, may be used as the hydrogen halide binding agent.

If this method is used to prepare a compound of the formula I wherein $R_3$ is quanidino, isothioureido or amidino with free amino groups, these amino groups must first be protected with a benzyl, benzhydryl or trityl substituent which is subsequently split off again by hydrogenation. The hydrogenation is preferably carried out in an organic solvent at a temperature between 0° and 150° C, preferably, however, at room temperature. Preferred solvents are polar organic solvents, such as alcohols, esters or dioxane. Suitable hydrogenation catalysts are especially noble metals, such as platinum or palladium, in finely divided form, for example deposited on carrier materials.

The compounds embraced by formula I form acid addition salts with inorganic or organic acids. Examples for non-toxic, pharmacologically acceptable acid addition salts are those formed with hydrochloric acid, hydrobromic acid, sulfuric acid, acetic acid, citric acid, laurylsulfonic acid, malic acid or the like.

The starting compound erythromycylamine of the formula II may be prepared by catalytic hydrogenation of erythromycin-oxime (see E. H. Massey et al, J. Med. Chem. 17, 105–107 [1974]).

The starting compounds of the formula IV, wherein W is cyano, may be prepared by addition of an unsaturated nitrile of the formula

wherein $R_1$ and $R_2$ have the meanings previously defined, to erythromycylamine (see R. Ryden et al, J. Med. Chem. 16, 1059–1060 [1973]).

The starting compounds of the formula IV, wherein W is nitro, may be prepared by addition of an unsaturated nitroalkylene of the formula

wherein $R_1$ and $R_2$ have the meanings previously defined, to erythromycylamine.

The starting compounds of the formulas III, V and VI are described in the literature or may be synthesized by methods described in the literature.

The starting compounds of the formula VII are obtained by condensaton of erythromycylamine with a ketoaldehyde of the formula

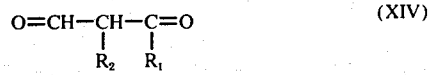

wherein $R_1$ and $R_2$ have the meanings previously defined. The starting compounds of the formula VIII are obtained by condensation of erythromycylamine with a diketone of the formula

wherein $R_1$ and $R_2$ have the meanings previously defined. The starting compounds of the formula IX are obtained by corresponding condensation with azomethine-ketones or -aldehydes of the formula

wherein $R_1$ and $R_2$ have the meanings previously defined, and $R_7$ is hydrogen, alkyl, hydroxyalkyl, phenylalkyl, phenyl, -A-B as defined above, thiazolyl, pyridyl, or $-NR_4R_5$ as defined above.

The starting compounds of the formula X are obtained by reduction of an N-cyano- or N-nitroalkyl-erythromycylamine of the formula IV with activated hydrogen, for instance in the presence of a finely divided metal, such as palladium, platinum or Raney nickel.

The guanidination agents used in method I, that is, 1-guanyl-3,5-dimethylpyrazole and the S-alkylisothiourea or O-alkyl-isourea salts, are described in the literature.

The starting compounds of the formula XI are also described in the literature or may be prepared by methods described in the literature, for example, by reaction of a urea, thiourea, carboxylic acid amide or dithiocarbamic acid ester with a halogenation agent, such as phosgene, thionyl chloride or phosphorus(V)chloride, in a non-polar solvent, such as benzene, toluene or 1,2-dichloro-ethane (see H. Ulrich, The Chemistry of Imidoyl Halides, Plenum Press, New York, 1968).

The following examples illustrate the present invention and will enable others skilled in the art to understand it more completely. It should be understood, however, that the invention is not limited solely to the particular examples given below.

Preparation of starting compounds

EXAMPLE A

N-(2-Nitro-ethyl)-erythromycylamine 7.34 gm of erythromycylamine (0.01 mol) were dissolved in 100 ml of absolute ethanol, and a solution of 750 mgm (0.012 mol) of nitroethylene in 20 ml of ethanol was added dropwise while cooling on ice. The resulting mixture was stirred at 0° C for half an hour, and subsequently the solvent was removed in vacuo. The residue was recrystallized in small portions from ethyl acetate/petroleum ether (1:3). Yield: 7.8 gm (96% of theory); m.p. 120° C (decomp.).

Elemental analysis: $C_{39}H_{73}N_3O_{14}$; Calculated: C-57.97%; H-9.11%; N-5.20%; Found: C-57.60%; H-9.12%; N-4.95%;

The following compounds were prepared in analogous manner:
a. N-(1-Methyl-2-nitro-ethyl)-erythromycylamine, decomp. 110°–115° C, from erythromycylamine and 1-nitro-propene.
b. N-(2-Nitro-propyl)-erythromycylamine, decomp. 120° C, from erythromycylamine and 2-nitro-propene.
N-([2-Nitro-1-phenyl]ethyl)-erythromycylamine, m.p. 145°–150 C, from erythromycylamine and nitrostyrene.

EXAMPLE B

N-(Formyl-methylene)-erythromycylamine

A solution of 150 mgm (0.002 mol) of glyoxal monohydrate in 10 ml of absolute ethanol was added dropwise to an ice-cooled solution of 1.47 gm (0.002 mol) of erythromycylamine in 30 ml of absolute ethanol. The resulting mixture was stirred at room temperature for 2 hours, and then the solvent was removed in vacuo. The desired compound was obtained as a colorless amorphous powder. M.p. decomp. above 125° C.

Elemental analysis: $C_{39}H_{70}N_2O_{13}$; (775.11); Calculated: C-60.43%; H-9.04%; N-3.61%; Found: C-60.11%; H-8.89%; N-3.37%;

The following compounds were prepared in analogous manner:
a. N-(Acetyl-methylene)-erythromycylamine, m.p. > 120° C (decomp.), from erythromycylamine and methylglyoxal.
b. N-(Benzoyl-methylene)-erythromycylamine, m.p. 136°–140° C, from erythromycylamine and phenylglyoxal.
c. N-(1-Acetyl-ethylidene)-erythromycylamine, m.p. 140°–145° C (decomp.), from erythromycylamine and diacetyl.
d. N-(1-Benzoyl-ethylidene)-erythromycylamine, m.p. decomp. above 154° C, from erythromycylamine and 1-phenyl-propanedione-1,2.
e. N-(2-Diethoxy ethylidene-1)-erythromycylamine, m.p. 117°–120° C, from erythromycylamine and glyoxal-semidiethylacetal.
f. N-(1-Diethoxy-propylidene-2)-erythromycylamine, m.p. 129°–130° C, from erythromycylamine and methylglyoxal-1,1-diethylacetal.
g. N-(1,3-Dioxane-2-yl-methylene)-erythromycylamine, m.p. 140°–142° C, from erythromycylamine and 1,3-dioxane-2-aldehyde.

EXAMPLE C

Diacetylphenylimine-erythromycylamine condensation product

A mixture of 735 mgm of erythromycylamine (0.001 mol), 160 mgm of diacetyl-monophenylimine and 50 ml of absolute ethanol was refluxed for 4 hours. A thin-layer chromatographic sample showed that the erythromycylamine had practically completely reacted. The solvent was removed in vacuo, and the residual vitreous product was purified by chromatography on a basic aluminum oxide column with methylene chloride/methanol (30:1) as the eluant. 280 mgm of the desired product were obtained ($R_f = 0.7$). Yield: 38% of theory; decomp. above 135° C.

Elemental analysis: $C_{45}H_{75}N_3O_{12}$; (850.23). Mass spectrum $M^+ = 849$ found.

EXAMPLE D

N-[2-(3,4,5-Trimethoxy-phenylimino)-ethylidene-1]-erythromycylamine

A mixture of 770 mgm of N-(formyl-methylene)-erythromycylamine (0.001 mol), 130 mgm of trimethoxyaniline (0.0012 mol) and 50 ml of ethanol was heated to 80° C. After about 9 hours of heating, no more starting compound could be found in the reaction mixture by thin-layer chromatography. The resulting solution was evaporated to dryness in vacuo, the residue was mixed with about 50 ml of ether, and the excess of trimethoxyaniline was filtered off. Subsequently, the ether was removed in vacuo. The residual vitrous mass was purified by column chromatography on basic aluminum oxide (methylene choride/methanol = 20:1). The desired product was obtained as the substance with the highest $R_f$-value. Yield: 390 mgm (42% of theory), decomp. above 160° C.

Elemental analysis: $C_{48}H_{81}N_3O_{15}$; mol.wt. calculated: 940.32; found $M^+$ 939 (MS); Calculated: C-61.31%; H-8.70%; N-4.47%; Found: C-60.88%; H-8.82%; N-4.19%.

EXAMPLE E

N-[2-(Hydroxyethylimino)-ethylidene-1]-erythromycylamine

A mixture of 1 gm of N-formylmethylene-erythromycylamine (0.0013 mol), 85 mg of ethanolamine and 50 ml of ethanol was heated at 80° C for 4 hours. The thin-layer chromatogram showed that the starting product had completely disappeared, and a new substance with an $R_f$-value of 0.65 (basic aluminum oxide; methylene chloride/methanol = 30:1) had formed. The solvent was removed in vacuo, and the obtained crude product was stirred together with a mixture of ether/petroleum ether = 1:1 and suction filtered. Yield: 760 mgm (73% of theory), m.p. 125°–130° C.

Elemental analysis: $C_{41}H_{75}N_3O_{13}$; mol.wt. 818.19; found $M^+$ 817 (MS); Calculated: C-60.18%; H-9.25%; N-5.14%; Found: C-60.44%; H-9.29%; N-4.97%.

The following compounds were synthesized analogous to Examples D and E:
a. N-(2-Methylimino-ethylidene)-erythromycylamine, m.p. 122° C, from N-formylmethylene-erythromycylamine and methylamine.
b. N-(2-Ethylimino-ethylidene)-erythromycylamine, m.p. 129°–135° C, from N-formylmethylene-erythromycylamine and ethylamine.
c. N-(2-Isopropylimino-ethylidene)-erythromycylamine, m.p. 136°–140° C, from N-formylmethylene-erythromycylamine and isopropylamine.
d. N-(2-Butylimino-ethylidene)-erythromycylamine, m.p. 132°–135° C, from N-formylmethylene-erythromycylamine and butylamine.
e. N-(2-Pentylimino-ethylidene)-erythromycylamine, m.p. 148°–149° C, from N-formylmethylene-erythromycylamine and pentylamine.
f. N-[2-(2'-Dimethylaminoethylimino)-ethylidene]-erythromycylamine, m.p. 151°–153° C, from N-formylmethlene-erythromycylamine and dimethylaminoethylamine.
g. N-[2-(2'-Ethoxyethylimino)-ethylidene]-erythromycylamine m.p. 160° C, from N-formylmethylene-erythromycylamine and ethoxyethylamine.

h. N-[(2-Carbomethoxymethylimino)-ethylidene]-erythromycylamine, m.p. 140° C, from N-formylmethylene-erythromycylamine and glycine methyl ester.

i. N-(2-Benzylimino-ethylidene)-erythromycylamine, m.p. 164° C, from N-formylmethylene-erythromycylamine and benzylamine.

j. N-[2-(α-Pyridylimino)-ethylidene]-erythromycylamine, m.p. 126°–130° C, from N-formylmethylene-erythromycylamine and α-aminopyridine.

k. N-(2-Phenylimino-ethylidene)-erythromycylamine, m.p. 141°–143° C, from N-formylmethylene-erythromycylamine and aniline.

l. N-[2-(Thiazolyl-2-imino)-ethylidene]-erythromycylamine, m.p. 157°–159° C, from N-formylmethylene-erythromycylamine and 2-amino-thiazole.

m. N-(3-Ethylimino-propylidene)-erythromycylamine, m.p. 134°–139° C, from N-formylethylidene-erythromycylamine and ethylamine.

EXAMPLE F

N-(1-Phenylhydrazono-ethylidene)-erythromycylamine

A mixture of 1.46 gm of erythromycylamine (0.002 mol) and 150 mgm of glyoxalmonophenylhydrazone (Chem. Ber. 59, 856) was heated in ethanol at 80° C until no more starting compound could be detected in the reaction solution by thin-layer chromatography (duration about 4 hours). The solvent was then removed in vacuo, and the residual vitreous mass was purified by chromatography on a basic aluminum oxide column with chloroform/methanol (20:1) as the eluant. The product with the highest $R_f$-value was the desired compound. Yield: 600 mgm (35% of theory); decomp. at 145° C Elemental analysis: $C_{45}H_{76}N_4O_{12}$ (881.25); Calculated: C-68.14%; H-8.71%; N-6.35%; Found: C-67.91%; H-8.70%; N-6.45%.

The following compound was prepared in analogous manner;

a. N-(2-Methylphenylhydrazone-ethylidene)-erythromycylamine, m.p. 122°–123° C, from erythromycylamine and glyoxalmethylphenylhydrazone.

EXAMPLE G

N-[2-(Thiomorpholinylimino)-ethylidene]-erythromycylamine 770 mgm of N-formylmethylene-erythromycylamine were dissolved in 40 ml of absolute ethanol, and the solution was stirred at room temperature with 150 mgm of N-amino-thiomorpholine for 4 hours. The solvent was then removed in vacuo, and the residue was admixed with 30 ml of ether. 400 mgm of the desired product crystallized out (45% of theory). $R_f = 0.7$ (basic aluminum oxide; chloroform/methanol = 30:1).

Elemental analysis: $C_{43}H_{78}N_4O_{12}$; mol.wt. 875.19; found: 874 (MS); Calculated: C-59.01%; H-8.98%; N-6.40%; S-3.66%; Found: C-58.80%; H-9.18%; N-6.44%; S-3.96%.

The following compounds were prepared in analogous manner:

a. N-(2-Hydrazono-ethylidene)-erythromycylamine, m.p. 152°–155° C, with hydrazine hydrochloride.

b. N-(2-Morpholinylimino-ethylidene)-erythromycylamine, m.p. 160°–165° C, with amino-morpholine.

c. N-[2-(Methylpiperazinyl-imino)-ethylidene]-erthromycylamine, m.p. 155°–165° C (decomp.), with N-amino-methylpiperazine.

d. N-(2-Piperidylimino-ethylidene)-erythromycylamine, m.p. 127°–130° C, with N-amino-piperidine.

e. N-(2-Dimethylhydrazono-ethylidene)-erythromycylamine, m.p. 142°–146° C, with N,N-dimethyl-hydrazine.

f. N-[2-(Thiomorpholinyl-S-oxide-imino)-ethylidene]-erythromycylamine, m.p. 132°–138° C, with N-amino-thiomorpholine-S-oxide.

g. N-[2-(Thiomorpholinyl-S,S-dioxide-imino)-ethylidene]-erythromycylamine, m.p. 146–149° C, with N-amino-thiomorpholine-S-dioxide.

Preparation of end products of the formula I

EXAMPLE 1

N-(1-Methyl-2-methoxy-ethyl)-erythromycylamine (I; $R_1 = CH_3$, $R_2 = H$, $R_3 = OCH_3$, $n = 0$) by method A 450 mgm of methoxyacetone were added to a solution of 1,46 gm of erythromycylamine (0.002 mol) in 50 ml of methanol. After stirring at room temperature for 2 hours, the components had completely reacted. The mixture was now cooled to 0° C, and an excess of sodium borohydride was added in small portions. The solution was then stirred for 2 hours and subsequently evaporated to dryness, the residue was taken up in water, and the aqueous solution was three times extracted with methylene chloride. The solvent was removed from the dried extracts, and the residual solid product was recrystallized from aqueous ethanol. Yield: 0.77 gm (46% of theory); m.p. >145° (decomp.).

Calculated: C-61.01%; H-9.76%; N-3.47%; Found: C-61.33%; H-9.50%; N-3.26%.

EXAMPLE 2

N-(2-Hydroxy-propyl)-erythromycylamine by method A 2.2 gm of erythromycylamine (0.003 mol) and 450 mgm of 2-hydroxy-propionaldehyde (0.006 mol) were dissolved in methanol, and 1 gm of sodium borohydride was added immediately, while cooling on ice. The mixture was allowed to react at 0° C for 2 hours, and was then worked up analogous to Example 1. The desired product was obtained in crystalline form by column-chromatographic purification (basic aluminum oxide; methylene chloride/methanol = 13:1). Yield: 450 mgm (20% of theory). Elemental analysis: $C_{40}H_{76}N_2O_{13}$ (793.06); mass spectrum $M^+ = 792$.

The following compounds were synthesized in analogoud manner:

a. N-(1-Phenyl-2-hydroxy-ethyl)-erythromycylamine, m.p. 127°–130° C, from erythromycylamine and oxyacetophenone.

b. N-(1-Methyl-2-phenyl-2-hydroxy-ethyl)-erythromycylamine, m.p. 144°–146° C, from erythromycylamine and 1-hydroxy-1-phenyl-2-propanone.

c. N-(1-Benzyl-2-hydroxy-ethyl)-erythromycylamine, m.p. 132°–138° C, from erythromycylamine and 1-phenyl-2-hydroxy-2-propanone.

d. N-(2,3-Dihydroxy-propyl)-erythromycylamine, m.p. 151°–153° C, from erythromycylamine and glycerin aldehyde.

e. N-(1-Methyl-2-diethylamino-ethyl)-erythromycylamine, decomp. above 122° C, from erythromycylamine and diethylamino-acetone.

f. N-(1-Methoxymethyl-2-methoxy-ethyl)-erythromycylamine, m.p. 111° C, from erythromycylamine and 1,3-dimethoxyacetone.

g. N-(1-Ethoxymethyl-2-ethoxy-ethyl)-erythromycylamine, m.p. 129°–130° C, from erythromycylamine and 1,3-diethoxyacetone.

h. N-(1-Phenyl-2-methoxy-ethyl)-erythromycylamine, decomp. above 150° C, from erythromycylamine and methoxy-acetophenone.

EXAMPLE 3

N-(2-Amino-ethyl)-erythromycylamine (I; $R_1 = R_2 =$ H, $R_3 = NH_2$, $n = 0$) by method B 1 gm of N-(2-nitro-ethyl)-erythromycylamine (0.0013 mol) were catalytically hydrogenated in 50 ml of ethanol in a closed vessel at a hydrogen pressure of 3 atmospheres and with 500 mgm of platinum oxide as the catalyst until hydrogen absorption had ceased. The catalyst was filtered off, and the filtrate was evaporated to dryness. By column chromatography (basic aluminum oxide; chloroform/methanol = 10:1) the desired product was obtained in crystalline form. $R_f$-value = 0.1; yield: 600 mgm (60% of theory); m.p. 130°–135° C (decomp.).

Elemental analysis: $C_{39}H_{75}N_3O_{12}$ (778.05); Calculated: C-60.20%; H-9.72%; N-5.40%; Found: C-60.20%; H-9.77%; N-5.08%;

The following compounds were synthesized in analogous manner from the corresponding nitro-substituted compound:

a. N-(2-Amino-1-methyl-ethyl)-erythromycylamine, m.p. 127°–130° C (decomp.).

b. N-(2-Amino-propyl)-erythromycylamine, m.p. 135°–140° C (decomp.).

c. N-(1-Phenyl-2-amino-ethyl)-erythromycylamine, m.p. 146°–150° C (decomp.).

EXAMPLE 4

N-(3-Amino-propyl)-erythromycylamine (I; $R_1 = R_2 =$ H, $R_3 = NH_2$, $n = 1$) by method B 1.58 gm (0.002 mol) of N-(2-cyano-ethyl)-erythromycylamine were dissolved in 200 ml of methanolic ammonia, and the solution was hydrogenated in an autoclave at 90° C for 4 hours at a hydrogen pressure of 100 atmospheres in the presence of 1.0 gm of Raney nickel.

Thereafter, the catalyst was filtered off, the solvent was removed from the filtrate in vacuo. and the residue was dissolved in aqueous 50% acetic acid. Nickel complexes possibly present were precipitated as nickel sulfide by introduction of hydrogen sulfide into the solution buffered with sodium acetate. The nickel sulfide precipitate was suction filtered off, the filtrate was adjusted to a pH-value of 7.3 with 2 N sodium hydroxide and extracted three times with methylene chloride, and the extracts were discarded. Subsequently, the aqueous solution was adjusted to a pH-value of 10 and again extracted three times with methylene chloride. The organic phases were combined, dried over sodium sulfate and evaporated. The residue was recrystallized from a mixture of ether and petroleum ether. White crystals were obtained. Yield: 1.16 gm (73% of theory); m.p. 120°–125° C.

Elemental anaylsis: $C_{40}H_{77}N_3O_{12}$ (792.08); Calculated: C-60.65%; H-9.80%; N-5.31%; Found: C-60.50%; H-9.92%; N-5.22%;

The following compounds were prepared in analogous manner:

a. N-(3-Amino-2-methyl-propyl)-erythromycylamine, m.p. 115°–118° C, from N-(2-cyanopropyl)-erythromycylamine and catalytically activated hydrogen.

b. N-(3-Amino-1-methyl-propyl)-erythromycylamine, m.p. 128°–132° C, from N-(2-cyano-1-methyl-ethyl)-erythromycylamine and catalytically activated hydrogen.

c. N-(3-Amino-1-phenyl-propyl)-erythromycylamine, m.p. 135°–140° C, from N-(2-cyano-1-phenyl-ethyl)-erythromycylamine and catalytically activated hydrogen.

EXAMPLE 5

N-(2-Hydroxy-ethyl)-erythromycylamine (I; $R_1 = R_2 =$ H, $R_3 = OH$, $n = 0$) by method D 770 mgm of N-(formylmethylene)-erythromycylamine were dissolved in 50 ml of ethanol, and the solution was hydrogenated in an autoclave at room temperature and a hydrogen pressure of 100 atmospheres in the presence of 0.5 gm of platinum oxide. After 6 hours the catalyst was filtered off, and the solvent was removed from the filtrate in vacuo. The pure product thus obtained began to decompose above 125° C. $R_f$-value = 0.3 (silicagel; dimethylformamide/methanol).

The same compound may also be prepared as follows:

An excess of sodium borohydride was added to an ice-cooled solution of 770 mgm of N-(formylmethylene)-erythromycylamine, and the mixture was stirred at 0° C for 6 hours. The erythromycylamine formed as a by-product was separated by preparative thick-layer chromatography (silicagel; dimethylformamide/methanol = 3:1). Yield: 200 mgm (30% of theory).

Elemental analysis: $C_{39}H_{74}N_2O_{13}$ (779.04); mass spectrum $M^+ = 778$; Calculated: C-60.12%; H-9.59%; N-3.60%; Found: C-60.24%; H-9.57%; N-3.42%;

The following compounds were prepared in analogous manner:

a. N-(2-Hydroxy-propyl)-erythromycylamine, m.p. 122°–125° C, from N-(acetylmethylene)-erythromycylamine.

b. N-(2-Hydroxy-2-phenyl-ethyl)-erythromycylamine, m.p. 138°–140° C, from N-(benzoylmethylene)-erythromycylamine.

c. N-(2-Hydroxy-1-methyl-propyl)-erythromycylamine, m.p. 126°–128° C, from N-(1-acetyl-ethylene)-erythromycylamine.

d. N-(2-Hydroxy-1-methyl-2-phenyl-ethyl)-erythromycylamine, m.p. 144–146° C, from N-(1-benzoyl-ethylidene)-erythromycylamine.

EXAMPLE 6

N-(2-[Thiomorpholinyl-amino]-ethyl)-erythromycylamine by method F 600 mgm of the condensation product of N-(formylmethylene)-erythromycylamine with N-amino-thiomorpholine (0.0006 mol) in 50 ml of methanol, were admixed with small portions of sodium borohydride while cooling on ice, until the starting compound could no longer be detected by thin-layer chromatography. The solvent was now removed in vacuo, the residue was taken up in water, and the aqueous solution was extracted three times with methylene chloride. After drying the combined extracts over sodium sulfate, the solvent was removed in vacuo. The residue was purified by column-chromatography on basic aluminum oxide with a mixture of methylene chloride and methanol (15:1) as the eluant. Yield: 230 mgm (37% of theory).

$R_f = 0.25$ (silicagel; methanol/dimethylformamide = 1:3). Mass spectrum $M^+ = 878$.

Elemental analysis: $C_{43}H_{82}N_4O_{12}S$ (879.16); Calculated: C-58.75%; H-9.40%; N-6.37%; Found: C-58.61%; H-9.34%; N-6.48%;

The following compounds were synthesized in analogous manner:

a. N-(2-Phenylamino-ethyl)-erythromycylamine, m.p. 164° C (decomp.), from the condensation product of N-(formylmethylene)-erythromycylamine with aniline.

b. N-(2-[3,4,5-Trimethoxyphenyl-amino]-ethyl)-erythromycylamine, decomp. >155° C, from the condensation product of N-(formylmethylene)-erythromycylamine and 3,4,5-trimethoxy-aniline.

c. N-(2-Methylamino-ethyl)-erythromycylamine, m.p. 128°–131° C (decomp.), by reduction of N-(2-methylimino-ethylidene)-erythromycylamine with sodium boranate.

d. N-(2-Ethylamino-ethyl)-erythromycylamine, m.p. 124°–126° C (decomp.), by reduction of N-(2-ethylimino-ethylidene)-erythromycylamine with sodium boranate.

e. N-(2-Isopropylamino-ethyl)-erythromycylamine, m.p. 125°–128° C (decomp.), by reduction of N-(2-isopropylimino-ethylidene)-erythromycylamine with sodium boranate.

f. N-(2-Butylamino-ethyl)-erythromycylamine, m.p. 123°–127° C (decomp.), by reduction of N-(2-butylimino-ethylidene)-erythromycylamine with sodium boranate.

g. N-(2-Pentylamino-ethyl)-erythromycylamine, m.p. 120°–122° C (decomp.), by reduction of N-(2-pentylimino-ethylidene)-erythromycylamine with sodium boranate.

h. N-[2-(2'-Hydroxyethyl-amino)-ethyl]-erythromycylamine, m.p. 129°–131° C (decomp.), by reduction of N-[2-(2'-hydroxyethylimino)-ethylidene]-erythromycylamine with sodium boranate.

i. N-[2-(2'-Dimethylaminoethyl-amino)-ethyl]-erythromycylamine, m.p. 127°–132° C (decomp.), by reduction of N-[2-(2'-dimethylaminoethylimino)-ethylidene]-erythromycylamine with sodium boranate.

j. N-[2-(Carbomethoxymethyl-amino)-ethyl]-erthyromycylamine, m.p. 131°–134° C (decomp.), by reduction of N-[2-(carbomethoxymethylimino)-ethylidene]-erythromycylamine with sodium boranate.

k. N-(2-Benzylaminoethyl)-erythromycylamine, m.p. 120°–130° C (decomp.), by reduction of N-(2-benzylimino-ethylidene)-erythromycylamine with sodium boranate.

l. N-[2-(Pyridyl-2-amino)-ethyl]-erythromycylamine, m.p. 130°–133° C (decomp.), by reduction of N-[2-(pyridyl-2-imino)-ethylidene]-erythromycylamine with sodium boranate.

m. N-[2-(Thiazolyl-2-amino)-ethyl]-erythromycylamine, m.p. 126°–130° C (decomp.), by reduction of N-[2-(thiazolyl-2-imino)-ethylidene]-erythromycylamine with sodium boranate.

n. N-[2-(N'-phenylhydrazino)-ethyl]-erythromycylamine, m.p. 135°–139° C (decomp.), by reduction of N-[2-(N'-phenylhydrazono)-ethylidene]-erythromycylamine with sodium boranate.

o. N-[2-(N',N'-Methylphenyl-hydrazino)-ethyl]-erythromycylamine, m.p. 132°–136° C (decomp.), by reduction of N-[2-(N',N'-methylphenylhydrazono)-ethylidene]-erythromycylamine with sodium boranate.

p. N-(2-Hydrazino-ethyl)-erythromycylamine, m.p. 139°–142° C (decomp.), by reduction of N-(2-hydrazino-ethylidene)-erythromycylamine with sodium boranate.

q. N-[2-(Morpholinyl-amino)-ethyl]-erythromycylamine, m.p. 133°–137° C (decomp.), by reduction of N-[2-(morpholinylimino)-ethylidene]-erythromycylamine with sodium boranate.

r. N-[2-(Methylpiperazinyl-amino)-ethyl]-erythromycylamine, m.p. 128°–133° C (decomp.), by reduction of N-[2-(methyl-piperazinyl-imino)-ethylidene]-erythromycylamine with sodium boranate.

s. N-[2-(Piperidinyl-amino)-ethyl]-erythromycylamine, m.p. 135°–137° C (decomp.), by reduction of N-[2-(piperidinylimino)-ethylidene]-erythromycylamine with sodium boranate.

t. N-[2-(N',N'-Dimethyl-hydrazino)-ethyl]-erythromycylamine, m.p. 138° C (decomp.), by reduction of N-[2-(N',N'-dimethyl-hydrazono)-ethylidene]-erythromycylamine with sodium boranate.

u. N-(3-Ethylamino-propyl)-erythromycylamine, m.p. 100°–120° C (decomp.), by reduction of N-(3-ethylimino-propylidene)-erythromycylamine with sodium boranate.

EXAMPLE 7

N-(3-Diethylamino-propyl)-erythromycylamine by method G 0.5 gm of palladium-on-charcoal were added to a solution of 0.79 gm (0.001 mol) of N-(3-amino-propyl)-erythromycylamine and 0.09 gm (0.002 mol) of acetaldehyde in 50 ml of absolute ethanol, and the mixture was hydrogenated at 25° C in an autoclave at a hydrogen pressure of 5 atmospheres for 17 hours.

After filtering off the catalyst, the alcohol was removed in vacuo, the residue was admixed with water, and the resulting suspension was adjusted to a pH-value of 9 with 1N sodium hydroxide and extracted three times with methylene chloride. The combined organic phases were dried over sodium sulfate and evaporated. The desired product was obtained in crystalline form by column-chromatography of the evaporation residue (basic aluminum oxide; chloroform/methanol = 20:1) and distilling off the eluant. Yield: 0.40 gm (47% of theory); m.p. 146°–148° C.

Elemental analysis: $C_{44}H_{85}N_3O_{12}$ (848.19); Calculated: C-62.31%; H-10.10%; N-4.95%; Found: C-62.24%; H-10.12%; N-4.98%;

The following compounds were prepared in analogous manner:

a. N-(3-Dimethylamino-propyl)-erythromycylamine, m.p. 125–135° C, by condensation of N-(3-amino-propyl)-erythromycylamine and formaldehyde (molar ratio = 1:2), and reduction of the resulting azomethine intermediate with catalytically activated hydrogen.

b. N-(3-Ethylamino-propyl)-erythromycylamine, m.p. 100°–120° C, by condensation of N-(3-amino-propyl)-erythromycylamine and acetaldehyde (molar ratio = 1:1), and reduction of the resulting azomethine intermediate with catalytically activated hydrogen.

c. N-(3-[2-Hydroxyethyl-amino]-propyl)-erythromycylamine, m.p. 133°–135° C, by condensation of N-(3-amino-propyl)erythromycylamine and glycol aldehyde (molar ratio = 1:1), and reduction of the resulting azomethine intermediate with catalytically activated hydrogen.

d. N-(3-Butylamino-propyl)-erythromycylamine, m.p. 119°–123° C (decomp.), by condensation of N-(3-amino-propyl)-erythromycylamine and butyraldehyde in the molar ration of 1:1 in the presence of catalytically activated hydrogen.

e. N-[3-(1,2-Dimethylpropyl-amino)-propyl]-erythromycylamine, m.p. 113°–116° C (decomp.), by condensation of N-(3-aminopropyl)-erythromycylamine and methyl isopropyl ketone in the molar ratio of 1:1 in the presence of catalytically activated hydrogen.

f. N-(3-Isopentylamino-propyl)-erythromycylamine, m.p. 110°–115° C (decomp.), by condensation of N-(3-amino-propyl)erythromycylamine and isovaleraldehyde in the molar ratio of 1:1 in the presence of catalytically activated hydrogen.

EXAMPLE 8

N-(3-Benzylamino-propyl)-erythromycylamine by method G

A solution of 0.79 gm (0.001 mol) of N-(3-amino-propyl)-erythromycylamine and 0.11 gm (0.001 mol) of benzaldehyde in 10 ml of absolute methanol was refluxed for 5 hours. Thereafter, the mixture was cooled to 0° C, 0.5 gm of sodium borohydride was added, and the resulting suspension was stirred at 25° C for 15 hours. Subsequently, the methanol was removed under reduced pressure, the residue was admixed with water, the aqueous mixture was acidified with hydrochloric acid, and the resulting solution was extracted three times with methylene chloride. The aqueous phase was adjusted to a pH-value of 10 with 1N sodium hydroxide and again extracted three times with methylene chloride. The combined organic extracts were dried over sodium sulfate and evaporated, and the solid residue was recrystallized from a mixture of ether and petroleum ether. White crystals were obtained. Yield: 0.54 gm (61% of theory); m.p. 125°–140° C.

Elemental analysis: $C_{47}H_{83}N_3O_{12}$ (882.207); Calculated: C-63.99%; H-9.48%; N-4.76%; Found: C-64.14%; H-9.60%; N-4.69%; The following compounds were prepared in analogous manner:

a. N-(2-Benzylamino-ethyl)-erythromycylamine, m.p. 120°–130° C, from N-(2-amino-ethyl)-erythromycylamine and benzaldehyde with sodium borohydride.

b. N-[3-(p-Chloro-benzylamino)-propyl]-erythromycylamine, m.p. 134°–142° C (decomp.), from N-(3-amino-propyl)-erythromycylamine and p-chlorobenzaldehyde with p-chlorobenzaldehyde with sodium borohydride.

c. N-[3-(p-Methoxy-benzylamino)-propyl]-erythromycylamine, m.p. 131°–136° C (decomp.), from N-(3-amino-propyl)-erythromycylamine and p-methoxybenz-aldehyde with sodium borohydride.

EXAMPLE 9

N-(3-[2-Hydroxy-propylamino]-propyl)-erythromycylamine by method C

A solution of 0.12 gm (0.002 mol) of propylene oxide in 20 ml of aqueous 50% methanol was added dropwise over a period of 12 hours to a solution of 0.79 gm (0.001 mol) of N-(3-amino-propyl)-erythromycylamine in 20 ml of aqueous 50% methanol at a temperature of 40° C, while stirring.

The solvent was then distilled off under reduced pressure, the residue was triturated with water, the aqueous mixture was extracted three times with methylene chloride, and the combined organic extracts were dried over sodium sulfate and evaporated. The desired product was obtained in crystalline form by column chromatography of the evaporation residue (basic aluminum oxide; chloroform/methanol = 20:1) and distilling off the eluant. Yield: 0.42 gm (49% of theory); m.p. 110°–115° C; Elemental analysis: $C_{43}H_{83}N_3O_{13}$ (850.16); Calculated: C-60.75%; H-9.84%; N-4.94%; Found: C-60.65%; H-9.92%; N-5.01%;

The following compounds were prepared in analogous manner:

a. N-(3-{Bis-[2-Hydroxypropyl-amino]}-propyl)-erythromycylamine, m.p. 108₁111° C, from N-(3-amino-propyl)-erythromycylamine and propylene oxide in the molar ratio of 1:8.

b. N-(3-[2-Hydroxyethyl-amino]-propyl)-erythromycylamine, m.p. 117°–123° C, from N-(3-amino-propyl)-erythromycylamine and ethylene oxide in the molar ratio of 1:2.

EXAMPLE 10

N-(3-Acetamido-propyl)-erythromycylamine by method H

A solution of 0.078 gm (0.001 mol) of acetyl chloride in 10 ml of absolute ether was added dropwise to a stirred solution of 0.79 gm (0.001 mol) of N-(3-amino-propyl)erythromycylamine in 25 ml of absolute ether, while keeping the temperature between 0° and +5° C by cooling. A crystalline precipitate was immediately formed.

The reaction mixture was stirred for another hour at +5° C, was then admixed with water, and the aqueous mixture was made alkaline (pH = 10), while cooling and vigorously stirring.

After separating the ether phase, the aqueous phase was extracted three times with ether. The combined organic solutions were dried over sodium sulfate and evaporated. The desired product was obtained in crystalline form by column chromatography of the evaporation residue (basic aluminum oxide; chloroform/methanol = 20:1) and removing the eluant. Yield: 0.47 gm (56% of theory); m.p. 104°–107° C.

Elemental analysis: $C_{42}H_{79}N_3O_{13}$ (834.12); Calculated: C-60.48%; H-9.55%; N-5.04%; Found: C-60.30%; H-9.60%; N-4.97%;

The following compounds were prepared in analogous manner:

a. N-(3-Formamido-propyl)-erythromycylamine, m.p. 116°–120° C, from N-(3-amino-propyl)-erythromycylamine and dimethylformamide-diethylacetal.

b. N-(2-Acetamido-ethyl)-erythromycylamine, m.p. 124°–130° C, from N-(2-amino-ethyl)-erythromycylamine and acetyl chloride.

c. N-(2-Benzamido-ethyl)-erythromycylamine, m.p. 146°–155° C, from N-(2-amino-ethyl)erythromycylamine and benzoyl chloride.

d. N-(2-[o-Methoxy-benzamido]-ethyl)-erythromycylamine, m.p. decomp. > 140° C, from N-(2-amino-ethyl)-erythromycylamine and o-methoxybenzoyl chloride.

e. N-(2-[o-Carboxy-benzamido]-ethyl)-erythromycylamine, m.p. decomp. > 165° C, from N-(2-aminoethyl)-erythromycylamine and phthalic acid anhydride.

f. N-(2-[2,4-Dichloro-benzamido]-ethyl)-erythromycylamine, m.p. decomp. > 150° C, from N-(2-amino-ethyl)-erythromycylamine and 2,4-dichlorobenzoyl chloride.

g. N-(2,6-Dichloro-phenylacetamido]-ethyl)-erythromycylamine, decomp. above 142° C, from N-(2-amino-ethyl)-erythromycylamine and 2,6-dichlorophenylacetyl chloride.

EXAMPLE 11

N-(3-p-Toluenesulfonamido-propyl)-erythromycylamine by method H

A solution of 0.19 gm (0.001 mol) of p-toluenesulfonic acid chloride in 10 ml of absolute ether was added dropwise to a stirred solution of 0.79 gm (0.001 mol) of*) triethylamine in 25 ml of absolute ether, while keeping the temperature between 0° and +5° C. A crystalline precipitate was formed. The reaction mixture was stirred for 1 hour more at +5° C, then suction-filtered, and the ether phase was washed with water, dried over sodium sulfate and evaporated. The solid residue was recrystallized from a mixture of ether and petroleum ether. Yield: 0.53 gm (57% of theory); m.p. above 140° C (decomp.).

*) N-(3-aminopropyl)-erythromycylamine and 0,7 gm (0,001 mol) of ...

Elemental analysis: $C_{47}H_{83}N_3O_{14}S$ (946.27); Calculated: C-59.66%; H-8.84%; S-3.39%; Found: C-59.58%; H-8.89%; S-3.50%;

The following compound was prepared in analogous manner:

N-(p-Toluenesulfonylamido-ethyl)-erythromycylamine, m.p. 136°–138° C (decomp.), from N-(2-amino-ethyl)-erythromycylamine and p-toluenesulfochloride.

EXAMPLE 12

N-{2-[(Dimethylamino)-(methylmercapto)-methyleneamino]-ethyl}-erythromycylamine by method J A solution of 210 mgm (0.0012 mol) of [dimethylaminomethylmercapto]-chlorocarbonium chloride in 10 ml of absolute methylene chloride was admixed at room temperature, while stirring and under exclusion of moisture, with a solution of 780 mgm (0.001 mol) of N-(2-amino-ethyl)-erythromycylamine and 0.3 gm (0.003 mol) of triethylamine in 20 ml of absolute methylene chloride, and the mixture was allowed to react for 2 hours. The reaction solution was then extracted three times with a small quantity of water, and the organic phase was dried over sodium sulfate and evaporated. The solid residue was purified by column chromatography on basic aluminum oxide (methylene chloride/methanol = 15:1). The desired compound was obtained as colorless crystals. Yield: 470 mgm (53% of theory); m.p. 110°–115° C (decomp.).

Elemental analysis: $C_{43}H_{82}N_4O_{12}S$ (879.23); Calculated: C-58.74%; H-9.40%; N-6.37%; Found: C-58.69%; H-9.47%; N-6.51%;

The following compounds were synthesized in analogous manner:

a. N-{2-[(Pyrrolidino)-(methylmercapto)-methyleneamino]-propyl}-erythromycylamine, m.p. 127° C (decomp.), from N-(2-amino-propyl)-erythromycylamine and [(pyrralidino-(methylmercapto)]-chlorocarbonium chloride.

b. . N-{2-[(N-Methylanilino)-(methylmercapto)-methyleneamino]-propyl}-erythromycylamine, m.p. 142°–145° C (decomp.), from N-(2-amino-propyl)-erythromycylamine and [(N-methylanilino)-(methylmercapto)]-chlorocarbonium chloride.

c. N-{2-[(Pyrrolidino)-2-cyanoethylmercapto)-methyleneamino]-propyl}-erythromycylamine, m.p. 131°–133° C (decomp.), from N-(2-amino-propyl)-erthromycylamine and [(pyrrolidino)-(2-cyanoethylmercapto)]-chlorocarbonium chloride.

d. N-{2-[(Dimethylamino)-(2-methoxyethylmercapto)-methyleneamino]-propyl}-erythromycylamine, m.p. 127°–130° C (decomp.), from N-(2-amino-propyl)-erythromycylamine and [(dimethyl-amino)-(2-methoxyethylmercapto)]-chlorocarbonium chloride.

e. N-{2-[(Dimethylamino)-(p-tolylmercapto)-methyleneamino]-propyl}-erythromycylamine, m.p. 130°–135° C (decomp.), from N-(2-amino-propyl)-erythromycylamine and [(dimethylamino)-(p-tolylmercapto)]-chlorocarbonium chloride.

f. N-{2-[(N-Methylanilino)-(p-tolylmercapto)-methyleneamino]-propyl}-erythromycylamine, m.p. 148°–150° C (decomp.), from N-(2-amino-propyl)-erythromycylamine and [(N-methylanilino)-(p-tolylmercapto)]-chlorocarbonium chloride.

g. N-{2-[(Pyrrolidino)-(benzylmercapto)-methyleneamino]-propyl}-erythromycylamine, m.p. 129°–130° C (decomp.), from N-(2-amino-propyl)-erythromycylamine and [(pyrrolidino)-(benzylmercapto)]-chlorocarbonium chloride.

h. N-{3-[(Pyrrolidino)-(methylmercapto)-methyleneamino]-propyl}-erythromycylamine, m.p. 116°–118° C (decomp.), from N-(3-amino-propyl)-erythromycylamine and [(pyrrolidino)-(methylmercapto)]-chlorocarbonium chloride.

i. N-{3-[(N-Methylanilino)-(methylmercapto)-methyleneamino]-propyl}-erythromycylamine, m.p. 124°–126° C (decomp.), from N-(3-amino-propyl)-erythromycylamine and [(N-methylanilino)-(methylmercapto)]-chlorocarbonium chloride.

j. N-{3-[(Pyrrolidino)-(benzylmercapto)-methyleneamino]-propyl}-erythromycylamine, m.p. 130° C (decomp.), from N-(3-amino-propyl)-erythromycylamine and [(pyrrolidino)-(benzylmercapto)]-chlorocarbonium chloride.

EXAMPLE 13

N-(3-Guanidino-propyl)-erythromycylamine by method I 1.58 gm (0.002 mol) of N-(3-amino-propyl)-erythromycylamine and 0.42 gm (0.002 mol) of 1-guanyl-3,5-dimethylpyrazole nitrate were dissolved in 50 ml of ethanol, and the solution was refluxed for 4 hours. Thereafter, the alcohol was distilled off in vacuo, the solid residue was dissolved in a small quantity of water, and the pH-value of the aqueous solution was adjusted to 9 by addition of 0.1 N sodium hydroxide. The mixture was extracted three times with methylene chloride, and the organic phase was dried over sodium sulfate and evaporated. The desired compound was obtained from the residue by column chromatography (basic aluminum oxide; chloroform/methanol = 13:3). Colorless crystals. Yield: 0.45 gm (27% of theory); m.p. 115° C (decomp.).

Elemental analysis: $C_{41}H_{79}N_5O_{12}$ (834.12); Calculated: C-59.04%; H-9.55%; N-8.39%; Found: C-59.15%; H-9.68%; N-8.26%;

EXAMPLE 14

N-[3-(N',N'-Dimethyl-guanidino)-propyl]-erythromycylamine by method J 2.1 gm (0.002 mol) of N-{3-[(dimethylamino)-(dibenzylamino)-methyleneamino]-propyl}-erythromycylamine were dissolved in 100 ml of ethanol and the solution was hydrogenated at room temperature in the presence of 4 gm of palladium-on-charcoal at atmospheric pressure. After 12 hours, the catalyst was filtered off, and the solvent was removed from the filtrate in vacuo. The pure product obtained as the residue was suspended in ether, filtered off and dried. Yield: 1.1gm (64% of theory); .p. 132°–136° C (decomp.).

Elemental analysis: $C_{43}H_{83}N_5O_{12}$ (862.18); Calculated: C-59.90%; H-9.70%; N-8.12%; Found: C-60.08%; H-9.81%; N-7.88%;

The following compound was synthesized in analogous manner:

N-[2-(N',N'-Tetramethylene-guandino)-ethyl]-erythromycylamino, m.p. 119°–121° C (decomp.), by catalytic reduction of N-{2-(dibenzylamino)-(pyrrolidinyl-1-methyleneamino]-ethyl}-etythromycylamine.

EXAMPLE 15

N-{3-[(Hexahydro-1H-azepine-1-yl)-(4-benzylpiperidyl-1)-methylene-amino]-propyl}-erythromycylamine by method J A solution of 0.42 gm (0.0012 mol) of [(hexahydro-1H-azepine-1-yl)-(4-benzylpiperidyl-1)]-chlorocarbonium chloride in 5 ml of methylene chloride was added dropwise to a solution of 0.79 gm (0.001 mol) of N-(3-amino-propyl)-erythromycylamine and 0.24 gm (0.0024 mol) of triethylamine in 10 ml of methylene chloride at a temperature of 0° C, while stirring and under exclusion of moisture. Subsequently, the reaction mixture was allowed to react at 0° C for 1 hour and then at room temperature for 2 hours. Thereafter, the reaction solution was washed with water, the organic phase was dried over sodium sulfate, and the solvent was distilled off in vacuo. The desired product was obtained in crystalline form by column chromatography of the evaporation residue (basic aluminum oxide; chloroform/methanol = 20:1). Yield: 0.66 gm (60% of theory); m.p. 121°–124° C (decomp.).

Elemental analysis: $C_{59}H_{103}N_5O_{12}$ (1074.51); Calculated: C-65.95%; H-9.66%; N-6.52%; Found: C-65.81%; H-9.74%; N-6.39%;

The following compounds were synthesized in analogous manner: [in these examples the starting compound N-(3-amino-propyl)-erythromycylamine is designated as A, N-(2-amino-ethyl)-erythromycylamine as B, and N-(2-amino-propyl)-erythromycylamine as C]:

a. N-{3-[(Hexahydro-1H-azepine-1-yl)-(ethylamino)-methyleneamino]-propyl}-erythromycylamine, m.p. 117°–120° C (decomp.). from A and [(hexahydro-1H-azepine-1-yl)-(ethyl-amino)]-chlorocarbonium chloride.

b. N-{3-[(Hexahydro-1H-azepine-1-yl)-(n-octylamino)-methyleneamino]-propyl}-erythromycylamine, m.p. 112°–115° C (decomp.). from A and [(hexahydro-1H-azepine-1-yl)-(n-octylamino)]-chlorocarbonium chloride.

c. N-{3-[(Hexahydro-1H-azepine-1-yl)-(benzhydrylamino)-methylene-amino]-propyl}-erythromycylamine, m.p. 131°–133° C (decomp.), from A and [(hexahydro-1H-azepine-1-yl)-(benzhydrylamino)]-chlorocarbonium chloride.

d. N-{3-[(Hexahydro-1H-azepine-1-yl)-(dimethylamino)-methyleneamino]-propyl}-erythromycylamine, m.p. 130° C (decomp.), from A and [(hexahydro-1H-azepine-1-yl)-(dimethylamino]-chlorocarbonium chloride.

e. N-{3-[(Hexahydro-1H-azepine-1-yl)-(diethylamino)-methyleneamino]-propyl}-erythromycylamine, m.p. 125°–128° C (decomp.), from A and [(hexahydro-1H-azepine-1-yl)-(diethylamino)]-chlorocarbonium chloride.

f. N-{3-[(Hexahydro-1H-azepine-1-yl)-(dibenzylamino)-methyleneamino]-propyl}-erythromycylamine, m.p. 137°–140° C (decomp.), from A and [(hexahydro-1H-azepine-1-yl)-(dibenzylamino)]-chlorocarbonium chloride.

g. N-{3-[(Hexahydro-1H-azepine-1-yl)-(pyrrolidinyl-1)-methyleneamino]-propyl}-erythromycylamine, m.p. 111°–114° C (decomp.), from A and [(hexahydro-1H-azepine-1-yl)-(pyrrolidinyl-1)]-chlorocarbonium chloride.

h. N-{3-](Hexahydro-1H-azepine-1-yl)-(piperidyl-1)-methyleneamino]-propyl}-erythromycylamine, m.p. 127°–130° C (decomp.), from A and ](hexahydro-1H-azepine-1-yl)-(piperidyl-1)]chlorocarbonium chloride.

i. N-{3-[Di-(hexahydro-1H-azepine-1-yl)-methyleneamino]propyl}-erythromycylamine, m.p. 122°–124° C (decomp.), from A and [di-(hexahydro-1H-azepine-1-yl)]-chlorocarbonium chloride.

j. N-{3-[(Hexahydro-1H-azepine-1-yl)-(N-methylanilino)methyleneamino]-propyl}-erythromycylamine, m.p. 115° C (decomp.), from A and [(hexahydro-1H-azepine-1-yl)-(Nmethylanilino)]-chlorocarbonium chloride.

k. N-{3-[(Hexahydro-1H-azepine-1-yl)-(4-methylpiperidyl-1)methyleneamino]-propyl}-erythromycylamine, m.p. 118°–120° C (decomp.), from A and [(hexahydro-1H-azepine-1-yl)-(4-methylpiperidyl-1)]-chlorocarbonium chloride.

l. N-{3-[(Benzylamino)-(dicyclohexylamino)-methyleneamino]propyl}-erythromycylamine, m.p. 136°–138° C (decomp.), from A and [(benzylamino)-dicyclohexylamino)]-chlorocarbonium chloride.

m. N-{3-[(Benzylamino)-(4-benzylpiperidyl-1)-methyleneamino]-propyl}-erythromycylamine, m.p. 105°–109° C (decomp.), from A and [(benzylamino)-(4-benzylpiperidyl-1)]-chlorocarbonium chloride.

n. N-{3-[(Benzylamino)-(hexahydro-1H-azepine-1-yl)-methyleneamino]-propyl}-erythromycylamine, m.p. 115°–118° C (decomp.), from A and [(benzylamino)-(hexahydro-1H-azepine-1-yl)]chlorocarbonium chloride.

o. N{3-[(Phenethylamino)-(hexahydro-1H-azepine-1-yl)-methyleneamino]-propyl}-erythromycylamine, m.p. 109°–112° C (decomp.), from A and [(phenethylamino)-(hexahydro-1H-azepine-1-yl)]-chlorocarbonium chloride.

p. N-{3-[(Phenoxyethylamino)-(hexahydro-1H-azepine-1-yl)methyleneamino]-propyl}-erythromycylamine, m.p. 118°–120° C (decomp.), from A and q. N-{3-[(Cyclohexylamino)-(hexahydro-1H-azepine-1-yl)methyleneamino]-propyl}-erythromycylamine, m.p. 119°–124° C (decomp.), from A and [(cyclohexylamino)-(hexahydro-1H-Hazepine-1-yl)]-chlorocarbonium chloride.

r. N-{3-[Bis-(dimethylamino)-methyleneamino]-propyl}-erythromycylamine, m.p. 110° C (decomp.), from A and [bis-(dimethylamino)]-chlorocarbonium chloride.

s. N-{3-[(Dimethylamino)-dibenzylamino)-methyleneamino]propyl}-erythromycylamine, m.p. 116°–119° C (decomp.), from A and [(dimethylamino)-(dibenzylamino)]-chlorocarbonium chloride.

t. N-{3-[(Dimethylamino)-(pyrrolidinyl-1)-methyleneamino]propyl}-erythromycylamine, m.p. 135° C (decomp.), from A and [(dimethylamino)-(pyrrolidinyl-1)]-chlorocarbonium chloride.

u. N-{3-[(Dimethylamino)-morpholinyl-4)-methyleneamino]propyl}-erythromycylamine, m.p. 125° C (decomp.), from A and [(dimethylamino)-(morpholinyl-4)]-chlorocarbonium chloride.

v. N-{3-[(Dimethylamino)-(N-methyl-anilino)-methyleneamino]propyl}-erythromycylamine, m.p. 134°–135° C (decomp.), from A and [(dimethylamino)-(N-methyl-anilino)]-chlorocarbonium chloride.

w. N-{3-[(Dibenzylamino)-(diethylamino)-methyleneamino]propyl}-erythromycylamine, m.p. 130° C (decomp.), from A and [(dibenzylamino)-(diethylamino)]-chlorocarbonium chloride.

x. N-{3-[(Dibenzylamino)-(bis-(2-methoxyethyl)-amino)-methyleneamino]-propyl}-erythromycylamine, m.p. 95° C (decomp.), from A and [(dibenzylamino)-(bis-(2-methoxyethyl)-amino)]chlorocarbonium chloride.

y. N-{3-[(Bis-(dibenzylamino)-methyleneamino]-propyl}-erythromycylamine, m.p. 141°–143° C (decomp.), from A and [bis-(dibenzylamino)]-chlorocarbonium chloride.

z. N-{3-[(Dibenzylamino)-(pyrrolidinyl-1)-methyleneamino]-propyl}-erythromycylamine, m.p. 125° C (decomp.), from A and [(dibenzylamino)-(pyrrolidinyl-1)]-chlorocarbonium chloride.

aa. N-{3-[(Dibenzylamino)-(piperidyl-1)-methyleneamino]-propyl}-erythomycylamine, m.p. 120°–123° C (decomp.), from A [(dibenzylamino)-(piperidyl-1)]-chlorocarbonium chloride.

ab. N-{3-[(Dibenzylamino)-(4-benzylpiperidyl-1)-methyleneamino]-propyl}-erythromycylamine, m.p. 118° C (decomp.), from A and [(dibenzylamino)-(4-benzylpiperidyl-1)]-chlorocarbonium chloride.

ac. N-{3-[(Dibenzylamino)-(morpholinyl-4)-methyleneamino]-propyl}-erythromycylamine, m.p. 123°–125° C (decomp.), from A and [(dibenzylamino)-(morpholinyl-4)]-chlorocarbonium chloride.

ad. N-{3-[(Dibenzylamino)-(4-methylpiperazinyl-1)-methyleneamino]-propyl}-erythromycylamine, m.p. 119°–122° C (decomp.), from A and [(dibenzylamino)-(4-methylpiperazinyl-1)]-chlorocarbonium chloride.

ae. N-{3-[(Dibenzylzmino)-(thiomorpholinyl-4)-methyleneamino]-propyl}-erythromycylamine, m.p. 129°–132° C (decomp.), from A and [(dibenzylamino)-(thiomorpholinyl-4)]-chlorocarbonium chloride.

af. N-{3-[(Dibenzylamino)-(N-methyl-anilino)-methyleneamino]-propyl}-erythromycylamine, m.p. 115° C (decomp.), from A and [(dibenzylamino)-(N-methyl-anilino)]-chlorocarbonium chloride.

ag. N-{3-[(N-Methyl-anilino)-(N-methyl-cyclohexylamino)-methyleneamino]-propyl}-erythromycylamine, m.p. 120° C (decomp.), from A and [(N-methyl-anilino)-(N-methyl-cyclohexylamino)]-chlorocarbonium chloride.

ah. N-{-3-[(N-Methyl-anilino)-pyrrolidinyl-1)-methyleneamino]-propyl}-erythromycylamine, m.p. 122°–125° C (decomp.), from A and [(N-methyl-anilino)-(pyrrolidinyl-1)]-chlorocarbonium chloride.

ai. N-{3-[Bis(N-methyl-anilino)-methyleneamino]-propyl}-erythromycylamine, m.p. 138°–140° C (decomp.) from A and [bis(N-methyl-anilino)]-chlorocarbonium chloride.

aj. N-{3-[(N-Benzyl-anilino)-(pyrrolidinyl-1)-methyleneamino]-propyl}-erythromycylamine, m.p. 117°–119° C (decomp.), from A and [(N-benzyl-anilino)-(pyrrolidinyl-1)]-chlorocarbonium chloride.

ak. N-{3-[(N-Benzyl-anilino)-(hexahydro-1H-azepine-1-yl)-methyleneamino]-propyl}-erythromycylamine, m.p. 123°–126° C (decomp.), from A and [(N-benzyl-anilino)-(hexahydro-1H-azepine-1-yl)]-chlorocarbonium chloride.

al. N-{3-[Bis-(4-benzylpiperidyl-1)-methyleneamino]-propyl}-erythromycylamine, m.p. 128°–130° C (decomp.), from A and [bis-(4-benzylpiperidyl-1)]-chlorocarbonium chloride.

am. N-{3-[(4-Benzylpiperidyl-1)-(pyrrolidinyl-1)-methyleneamino]-propyl}-erythromycylamine, m.p. 122° C (decomp.), from A and [(4-benzylpiperidyl-1)-(pyrrolidinyl-1)]-chlorocarbonium chloride.

an. N-{2-[(Benzylamino)-(dimethylamino)-methyleneamino]-ethyl}-erythromyclylamine, m.p. 118°–119° C (decomp.), from B and [(benzylamino)-(dimethylamino)]-chlorocarbonium chloride.

ao. N-{2-[(Benzylamino)-(diethylamino)-methyleneamino]-ethyl}-erythromycylamine, m.p. 116°–118° C (decomp.), from B and [(benzylamino-(diethylamino)]-chlorocarbonium chloride.

ap. N-{2-[(Benzylamino)-(diisopropylamino)-methyleneamino]-ethyl}-erythromycylamino, m.p. 111°–112° C (decomp.), from B and [(benzylamino)-(diisopropylamino)]-chlorocarbonium chloride.

aq. N-{2-[(Benzylamino)-(di-(2-methoxyethyl)-amino)-methyleneamino]-propyl}-erythromycylamine, m.p. 109°–111° C (decomp.), from C and [(benzylamino)-(di-(2-methoxyethyl)-amino)]-chlorocarbonium chloride.

ar. N-{2-[(Benzylamino)-(thiomorpholinyl-4)-methyleneamino]-propyl}erythromycylamine, m.p. 121°–124° C (decomp.), from C and [(benzylamino)-(thiomorpholinyl-4)-chlorocarbonium chloride.

as. N-{2-[(benzylamino-(N-ethyl-cyclohexylamino)-methyleneamino]-ethyl}-erythromycylaine, m.p. 119°–124° C (decomp.), from B and [(benzylamino)-(N-ethyl-cyclohexylamino)]-chlorocarbonium chloride.

at. N-{2-[(Benzylamino)-(N-phenyl-benzylamino)-methyleneamino]-ethyl}-erythromycylamine, m.p. 126°–128° C (decomp.), from B and [(benzylamino)-

(N-phenyl-benzylamino)]-chlorocarbonium chloride.

au. N-{2-[(Benzylamino)-(4-benzylpiperazinyl-1)-methyleneamino]-ethyl}-erythromycylamine, m.p. 117°–119° C (decomp.), from B and [(benzylamino)-(4-benzylpiperazinyl-1)]-chlorocarbonium chloride.

av. N-{2-[(Benzylamino)-(N-methyl-benzylamino)-methyleneamino]-ethyl}-erythromycylamine, m.p. 128°–130° C (decomp.), from B and [(benzylamino)-(N-methyl-benzylamino)]-chlorocarbonium chloride.

aw) N-{2-[(Benzylamino)-(N-ethyl-benzylamino)-methyleneamino]-ethyl}-erythromycylamine, m.p. 122°–123° C (decomp.), from B and [(benzylamino)-(N-ethyl-benzylamino)]-chlorocarbonium chloride.

ax N-{2-[(Pyrrolidinyl-1)-(ethylamino)-methyleneamino]-propyl}-erythromycylamine, m.p. 110°–111° C (decomp,), from C and [(pyrrolidinyl-1-(ethylamino)]-chlorocarbonium chloride.

ay N-{2-[(Pyrrolidinyl-1-(diethylamino)-methyleneamino]-propyl}-erythromycylamine, m.p. 107°–108° C (decomp.), from C and [(pyrrolidinyl-1)-(diethylamino)]-chlorocarbonium chloride.

az) N-{2-[(Pyrrolidinyl-1)-(n-butylamino)-methyleneamino]-propyl}-erythromycylamine, m.p. 113° C (decomp.), from C and [(pyrrolidinyl-1)-(n-butylamino)]-chlorocarbonium chloride.

ba) N-{2-[(Pyrrolidinyl-1)-(tert.butylamino)-methylenamino]-propyl}-erythromycylamine, m.p. 106°–109° C (decomp.), from C and ](pyrrolidinyl-1)-(tert.butylamino)]-chlorocarbonium chloride.

bb) N-{2-[Di-(pyrrolidinyl-1)-methyleneamino]-propyl}-erythromycylamine, m.p. 104°–110° C (decomp.), from C and [di-(pyrrolidinyl-1)]-chlorocarbonium chloride.

bc) N-{2-[(Pyrrolidinyl-(cyclohexylamino)-methyleneamino]-propyl}-erythromycylamine, m.p. 116°–119° C (decomp.), from C and [(pyrrolidinyl-1-)-(cyclohexylamino)]-chlorocarbonium chloride.

bd) N-{2-[(Pyrrolidinyl-1)-(3,4,5-trimethoxybenzylamino)methyleneamino]-propyl}-erythromycylamine, m.p. 24°-127° C (decomp.), from C and [(pyrrolidinyl-1)-(3,4,5-trimethoxybenzylamino)]-chlorocarbonium chloride.

be) N-{2-[(Pyrrolidinyl-1)-(4-benzylpiperidyl-1)-methyleneamino] -propyl} -erythromycylamine, m.p. 120° C (decomp.), from C and [(pyrrolidinyl-1)-4-benzylpiperidyl-1(]-chlorocarbonium chloride.

bf) N{2-[(N-Methyl-anilino)-(dimethylamino)-methyleneamino]-ethyl}-erythromycylamine, m.p. 129°-132° C (decomp.), from B and [(N-methyl-anilino)-(dimethylamino)]-chlorocarbonium chloride.

bg) N-{2-[(Cyclohexylamino)-(dicyclohexylamino)-methyleneamino]-propyl}-erythromycylamine, m.p. 126°127° C (decomp.), from C and [cyclohexylamino)-(dicyclohexylamino)]-chlorocarbonium chloride.

bh) N-{2-[(Cyclohexylamino)-(4-benzylpiperidyl-1)-methyleneamino]-propyl}-erythromycylamine, m.p. 124–125° C (decomp.), from C and [(cyclohexylamino)-(4-benzylpiperidyl-1)]chlorocarbonium chloride.

bi) N-{2-[(4-Benzylpiperidyl-1-(n-butylamino)-methyleneamino]-ethyl}-erythromycylamine, m.p. 119°–120° C (decomp.), from B and [(4-benzylpiperidyl-1)-(n-butylamino)]-chlorocarbonium chloride.

bj) N-{2-[(4-Benzylpiperidyl-1)-(tert.butylamino)-methyleneamino]-ethyl}-erythromycylamine, m.p. 113–116° C (decomp.), from B and [(4-benzylpiperidyl-1)-(tert.butylamino)]-chlorocarbonium chloride.

bk) N-{2-[(4-Benzylpiperidyl-1)-(dicyclohexylamino)-methylene-amino]-ethyl}-erythromycylamine, m.p. 125–132° C (decomp.), from B and [(4-benzylpiperidyl-1)-(dicyclohexylamino)]chlorocarbonium chloride.

EXAMPLE 16

N-{3-[(Furyl-2)-(pyrrolidinyl-1)-methyleneamino]-propyl}-erythromycylamine by method J A solution of 0.66 gm (0.003 mol) of [(furyl-2)-(pyrrolidinyl-1)]-chlorocarbonium chloride in 10 ml of methylene chloride was added at room temperature, while stirring and under exclusion of moisture, to a solution of 1.58 gm (0.002 mol) of N-(3-aminopropyl)-erythromycylamine and 0.6 gm (0.006 mol) of triethylamine in 20 ml of methylene chloride.

The mixture was allowed to react at the same temperature for half an hour. Thereafter, the solvent was distilled off in vacuo, and the desired product was isolated from the solid distillation residue by column chromatography (basic aluminum oxide; chloroform/methanol = 75:1). Yield: 0.67 gm (36% of theory); m.p. 95°–100° C (decomp.).

Elemental analysis: $C_{49}H_{86}N_4O_{13}$ (939.26); Calculated: C-62.65%; H-9.22%; N-5.96%; Found: C-62.81%; H-9.29%; N-6.08%;

The following compounds were synthesized in analogous manner: (in these examples A, B and C designate the same starting compounds as in Examples 15a - bk).

a. N-{3-[(Dimethylamino)-methyleneamino]-propyl}-erythromycylamine, m.p. 124° C (decomp.), from A and (dimethylamino) -chlorocarbonium chloride.

b. N-{3-[(N-Benzylmethylamino)-methyleneamino]-propyl}-erythromycylamine, m.p. 121–123° C (decomp.), from A and (N-benzylmethylamino)-chlorocarbonium chloride.

c. N-{3-[(Pyrrolidinyl-1)-methyleneamino]-propyl}-erythromycylamine, m.p. 118–120° C (decomp.), from A and (pyrrolidinyl-1)-chlorocarbonium chloride.

d. N-{3-[(Piperidyl-1)-methyleneamino]-propyl}-erythromycylamine, m.p. 121° C (decomp.), from A and (piperidyl-1)-chlorocarbonium chloride.

e. N-{3-[(Hexahydro-1H-azepine-1-yl)-methyleneamino]-propyl}-erythromycylamine, m.p. 120–123° C (decomp.), from A and (hexahydro-1H-azepine-1-yl)-chlorocarbonium chloride.

f. N-{3-[(Morpholinyl-4)-methyleneamino]-propyl}-erythromycylamine, m.p. 124° C (decomp.), from A and (morpholinyl-4)-chlorocarbonium chloride.

g. N-{3-[1-(Dimethylamino)-ethylideneamino]-propyl}-erythromycylamine, m.p. 120° C (decomp.), from A and [(dimethylamino)-(methyl)]-chlorocarbonium chloride.

h. N-{3-[1-(diethylamino)-ethylideneamino]-propyl}-erythromycylamine, m.p. 103° C (decomp.), from A and [(diethylamino)-(methyl)]-chlorocarbonium chloride.

i. N-{3-[1-(N-Benzyl-methylamino)-ethylideneamino]-propyl}-erythromycylamine, m.p. 118–120° C (decomp.), from A and [(N-benzyl-methylamino)-(methyl)]-chlorocarbonium chloride.

j. N-{3-[1-(Pyrrolidinyl-1)-ethylideneamino]-propyl}-erythromycylamine, m.p. 124–126° C (decomp.), from A and [(pyrrolidinyl-1)-(methyl)]-chlorocarbonium chloride.

k. N-{3-[1-(Hexahydro-1H-azepine-1-yl)-ethylideneamino]-propyl}-erythromycylamine, m.p. 132–134° C (decomp.), from A and [(hexahydro-1H-azepine-1-yl)-(methyl)]-chlorocarbonium chloride.

l. N-{3-[1-(Diethylamino-butylideneamino]-propyl}-erythromycylamine, m.p. 123° C (decomp.), from A and [(diethylamino)-(propyl)]-chlorocarbonium chloride.

m. N-{3-[1-(Di-(2-methoxyethyl)amino)-butylideneamino]propyl}-erythromycylamine, m.p. 111–114° C (decomp.), from A and [(di-(2-methoxyethyl)amino)-(propyl)]-chlorocarbonium chloride.

n. N-{3-[1-(Pyrrolidinyl-1)-butylideneamino]-propyl}-erythromycylamine, m.p. 128–130° C (decomp.), from A and [(pyrrolidinyl-1)-(propyl)]-chlorocarbonium chloride.

o. N-{3-[1-(Diethyl-amino)-2-phenyl-ethylideneamino]-propyl}-erythromycylamine, m.p. 105–107° C (decomp.), from A and [(diethylamino)-(benzyl)]-chlorocarbonium chloride.

p. N-{3-[1-(Dibenzylamino)-2-phenyl-ethylideneamino]-propyl}-erythromycylamine, m.p. 116–118° C (decomp.), from A and [(dibenzylamino)-(benzyl)]-chlorocarbonium chloride.

q. N-{3-[1-(Pyrrolidinyl-1)-2-phenyl-ethylideneamino]-propyl}-erythromycylamine, m.p. 12–128° C (decomp.), from A and [(pyrrolidinyl-1)-(benzyl)]-chlorocarbonium chloride.

r. N-{3-[1-(Hexahydro-1H-azepine-1-yl)-2-phenyl-ethylideneamino]-propyl}-erythromycylamine, m.p. 114–117° C (decomp.), from A and [(hexahydro-1H-azepine-1-yl)-(benzyl)]-chloro-carbonium chloride.

s. N-{3-[α-(Diethylamino)-benzylideneamino]-propyl}-erythromycylamine, m.p. 190–112° C (decomp.), from A and [(di-ethylamino)-(phenyl)]-chlorocarbonium chloride.

t. N-{3-[α-(Pyrrolidinyl-1)-benzylideneamino]-propyl}-erythromycylamine, m.p. 132° C (decomp.), from A and [(pyrrolidinyl-1)-(phenyl)]-chlorocarbonium chloride.

u. N-{3-[α-(Pyrrolidinyl-1)-(o-methoxy)-benzylideneamino]-propyl}-erythromycylamine, m.p. 132–134° C (decomp.), from A and [(pyrrolidinyl-1)-(o-methoxyphenyl)]-chlorocarbonium chloride.

v. N-{3-[(Diethylamino)-(thienyl-2)-methyleneamino]-propyl}erythromycylamine, m.p. 117–118° C (decomp.), from A and [(diethylamino)-(thienyl-2)]-chlorocarbonium chloride.

w. N-{3-[(Pyrrolidinyl-1)-(thienyl-2)-methyleneamino]-propyl}-erythromycylamine, m.p. 133–135° C (decomp.), from A and [(pyrrolidinyl-1)-(thienyl-2)]-chlorocarbonium chloride.

x. N-{3-[(Pyridyl-3)-(pyrrolidinyl-1)-methyleneamino]-propyl}-erythromycylamine, m.p. 112° C (decomp.), from A and [(pyridyl-3)-(pyrrolidinyl-1)]-chlorocarbonium chloride.

y. N-{2-[(Heptahydro-1H-azocine-1-yl)-methyleneamino]-ethyl}-erythromycylamine, m.p. 118–119° C (decomp.), from B and (heptahydro-1H-azocine-1-yl)-chlorocarbonium chloride.

z. N-{2-[(Hexahydro-1H-azepine-1-yl)-methyleneamino]-propyl}-erythromycylamine, m.p. 114–116° C (decomp.), from C and (hexahydro-1H-azepine-1-yl)-chlorocarbonium chloride.

aa. N-{2-[(Cyclohexyl)-(pyrrolidinyl-1) methyleneamino]-ethyl}-erythromycylamine, m.p. 121–122° C (decomp.), from B and [(cyclohexyl)-(pyrrolidinyl-1)]-chlorocarbonium chloride.

ab. N-{2-[(Benzylamino)-(cyclohexyl)-methyleneamino]-ethyl}-erythromycylamine, m.p. 117° C (decomp.), from B and [(benzylamino)-(cyclohexyl)]-chlorocarbonium chloride.

ac. N-{2-[(Cyclohexyl)-(m,p-dimethoxybenzylamino)-methyleneamino]-ethyl}-erythromycylamine, m.p. 128–130° C (decomp.), from B and [(cyclohexyl)-(m,p-dimethoxybenzylamino)]-chlorcarbonium chloride.

ad. N-{2-[1-(Diethylamino)-2-phenyl-ethylideneamino]-ethyl}erythromycylamine, m.p. 117–119° C (decomp.), from B and [(diethylamino)-benzyl]-chlorocarbonium chloride.

ae. N-{2-[1-(m,p-Dimethoxybenzylamino)-2-phenyl-ethylideneamino]-ethyl}-erythromycylamine, m.p. 124–128° C (decomp.), from B and [(m,p-dimethoxy-benzylamino)-benzyl]-chlorocarbonium chloride.

EXAMPLE 17

N-[2-(2'-Ethoxyethyl-amino)-ethyl]-erythromycylamine by method F

Sodium borohydride was added in small portions in a solution of 1.64 gm (0.002 mol) of N-[2-(2'-ethoxyethylamino)-ethylidene]-erythromycylamine in 50 ml of methanol, while cooling on ice, until the reaction had gone to completion as determined by thin-layer chromatography.

The solvent was then distilled off in vacuo, the residue was admixed with water, and the aqueous mixture was extracted with methylene chloride. After drying the organic phase over sodium sulfate and evaporating it, the desired product was obtained by column chromatography of the evaporation residue (basic aluminum oxide; methylene chloride/methanol = 15:1). Yield: 0.92 gm (56% of theory); m.p. 124–127° C (decomp.).

Elemental analysis: $C_{43}H_{83}N_2O_{12}$ (820.15); Calculated: C-62.97%; H-10.20%; N-3.41%; Found: C-63.06%; H-10.27%; N-3.29%;

The following compounds were prepared in analogous manner:

a. N-[2-(2'-Dimethylamino-ethyl-amino)-ethyl]-erythromycylamine, m.p. 127–132° C (decomp.), from N-[2-(2'-diemthylamino-ethylamino)-ethylidene]-erythromycylamine.

b. N-[2-(Carbomethoxymethylamino)-ethyl]-erythromycylamine, m.p. 131–134° C (decomp.), from N-[2-(carbomethoxymethylimino)-ethylidene]-erythromycylamine.

c. N-[2-(Pyridyl-2-amino)-ethyl]-erythromycylamine, m.p. 130–133° C (decomp.), from N-[2-(pyridyl-2-imino)-ethyl-idene]-erythromycylamine.

d. N-[2-(Thiazolyl-2-amino)-ethyl]-erythromycylamine, m.p. 126–130° C (decomp.), from N-[2-(thiazolyl-2-imino)-ethylidene]-erythromycylamine.

The compounds of the present invention have useful pharmacological properties. More particularly, they exhibit antibacterial activity against gram-positive and gram-negative bacteria, such as Staph.aureus SG 511, Strep-aronson and E. coli.

The antibacterial activity of the compounds of this invention was ascertained by means of the agar-diffusion test and the series dilution test in analogy to the respective methods described by P. Klein In "Bakteriologische Grundlagen der Chemotherapeutischen Laboratoriumspraxis", pages 53–76 and 87–109, published by Springer-Verlag, Stuttgart, Germany (1957).

For example, these test showed that the following compounds still exhibited very effective antibacterial activity against Staph. aureus SG 511 and Strep.aronson at concentrations of 0.3 to 5 μgm/ml, and against E. coli at concentrations to 10 to 40 μgm/ml:

N-(3-Ethylaminopropyl)-erythromycylamine,
N-(3-Benzylaminopropyl)-erythromycylamine,
N-(3-[2-Hydroxypropylamino]propyl)-erthromycylamine,
N-(3-{Bis-[2-hydroxypropylamino]-}propyl)-erthromycylamine,
N-(3-Formylaminopropyl)-erythromycylamine,
N-(2-Hydroxyethyl)-erythromycylamine,
N-([3-(p-Chloro)-benzylaminopropyl]-erythromycylamine,
N-([3(-p-Methoxy)-benzylaminopropyl]-erythromycylamine,
N-(2-Aminoethyl)-erythromycylamine,
N-([1-Methyl-2-methoxy]-ethyl)-erythromycylamine
N-(2-Tosylaminoethyl)-erythromycylamine,
N-([1-Methoxymethyl-2-methoxy]ethyl)-erythromycylamine,
N-{3-[(Hexahydro-1H-azepine-1y1)-(n-octylamino)-methyleneamino]-propyl}-erythromycylamine,
N-{3-[(Benzylamino)-(4-benzylpiperridyl-1)-methyleneamino]- propyl}-erythromycylamine,
N-{3-[(Dibenzylamino)-(4-benzylpiperidyl1)-methyleneamino]- propyl}-erythromcyclamine,
N-{3-[(Furyl2)-(pyrrolindinyl1)-methyleneamino]-propyl}- erythromycylamine,
N-{3[α-(Diethylamino)-benzylideneamino]-propyl}-erythromycylamine,
N-{3-[1-(Hexahydro-1H-azepine-1-yl)-2-phenyl-ethylideneamino]- propyl}-erythromycylamine,
N-{2-[(Pyrrolidinyl-1)-(4-benzylpiperidyl-1)-methyleneamino]- propyl}-erythromycylamine,
N-{3-[(N-Benzylmethylamino)-methyleneamino]-propyl}-erythromycylamine,
N-{3-[(Hexahydro-1H-azepine-1yl)-methyleneamino]-propyl}- erythromycylamine,
N- 2(Morpholinylamino)-ethyl]-erythromycylamine,
N-{3-[Bis-(4benzylpiperidyl-1)-methyleneamino]-propyl}- erythromycylamine,
N-{3-[(Di-(2-methoxyethyl)amino)-butylideneamino]-propyl}-erythromycylamine,
N-2-[-(Diethylamino)-2-phenyl-ethylideneamino]-ethyl-ery- thromycylamine,
N-[2-(2'-Ethoxyethylamino)-ethyl]-erythromycylamine,
N-[2-(Carbomethoxymethylamino)-ethyl]-erythromycylamine,
N-[2-(Pyridyl-2-amino)-ethyl]-erythromycylamine, and
N-[2-(Thiazolyl-2-amino)-ethyl]-erythromycylamine.

The acute toxicity of the compounds of this invention was determined in the mouse. After oral and subcutaneous application all of these compounds showed $LD_{50}$-values >1gm/kg mouse.

For pharmaceutical purposes the compounds according to the present invention are administered to warm-blooded animals perorally or parenterally, but preferably perorally, as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. One effective antibacterial oral dosage unit of the compounds according to the present invention is from 0.83 to 8.3 mgm/kg body weight, preferably 1.6 to 4.2 mgm/kg body weight. The daily dose rate is from 8.3 to 66.7 mgm/kg, preferably 16.6 to 33.3 mgm/kg.

The following examples illustrate a few antibacterial pharmaceutical oral dosage unit compositions comprising a compound of the present invention as an active ingredient and represent the best modes contemplated of putting the invention into practical use. The parts are parts by weight unless otherwise specified.

EXAMPLE 18

TABLETS

The tablet composition is compounded from the following ingredients:

| | |
|---|---|
| N-(3-Ethylamino-propyl)-erythromycylamine | 100.0 parts |
| Lactose | 63.0 parts |
| Potato starch | 50.0 parts |
| Polyvinylpyrrolidone | 5.0 parts |
| Magnesium stearate | 2.0 parts |
| Total | 220.0 parts |

PREPARATION

The active ingredient, the lactose and the potato starch are intimately admixed with each other, the mixture is moistened with an aqueous 10% solution of the polyvinylpyrrolidone, the moist mass is granulated through a 1.5mm-mesh screen, the granulate is dried at 45 C and again passed through the screen, and the dry granulate is admixed with the magnesium tearate. The resulting composition is compressed into 220 mgm-tablets, each of which contains 100 mgm of active ingredient.

EXAMPLE 19

Coated pills

The pill core composition is compounded from the following ingredients:

| | |
|---|---|
| N-(3-Ethylamino-propyl)-erythromycylamine | 100.0 parts |
| Lactose | 30.0 parts |
| Corn starch | 30.0 parts |
| Gelatin | 3.0 parts |
| Cellulose, microcrystalline | 6.0 parts |
| Magnesium stearate | 1.0 parts |
| Total | 170.0 parts |

Preparation

The active ingredient, the lactose and the corn starch are thoroughly admixed with each other, the mixture is moistened with an aqueous 12% solution of the gelatin, the moist mass is granulated through a 1.5 mm-mesh screen, and the granulate is dried at 45 C and again passed through a 1.0 mm-mesh screen. The dry granulate is admixed with the cellulose and the magnesium stearate, and the resulting composition is compressed into 170 mgm-pill cores, which are subsequently coated with a thin shell consisting essentially of a mixture or sugar and talcum, and finally polished with beeswax. Each pill contains 100 mgm of active ingredient.

Example 20

Suspension

The suspension is compounded from the following ingredients:

| | |
|---|---|
| N-(3-Benzylamino-propyl)-erythromycylamine | 1.0 parts |
| Sorbitol monopalmitate (Span 40) | 1.0 parts |
| Polyglycolether emulsifier (Cremophor O) | 2.0 parts |
| Cetyl stearyl alcohol (Lanette O) | 2.0 parts |
| Cetaceum | 1.0 parts |
| Decyloleate | 5.0 parts |
| Paraffin oil | 1.0 parts |
| Distilled water | 87.0 parts |
| Total | 100.0 parts |

Preparation

The ingredients, with the exception of the active ingredient and the distilled water, are admixed with each other, the mixture is melted, and the molten mass is heated to 70° C and then emulsified in the distilled water at 70° C. The aqueous emulsion is cooled to 40° C, and the active ingredient is uniformly suspended therein with the aid of an immersion homogenizer. The finished suspension is cooled to room temperature. 100gm of the suspension contain 1gm of the active ingredient.

Any one of the other compounds embraced by formula I or a non-toxic acid addition salt thereof may be substituted for the particular erythromycylamine derivative in Examples 18 through 20. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certian specific embodiments thereof, it will be readily apparent to others skilled in the art that the invention is not limited to these particular embodiments, and that various changes and modifications may be made without departing from the spirit of the invention or the scope of the appended claims.

We Claim:

1. A compound of the formula

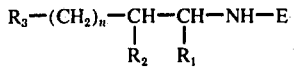

wherein E is

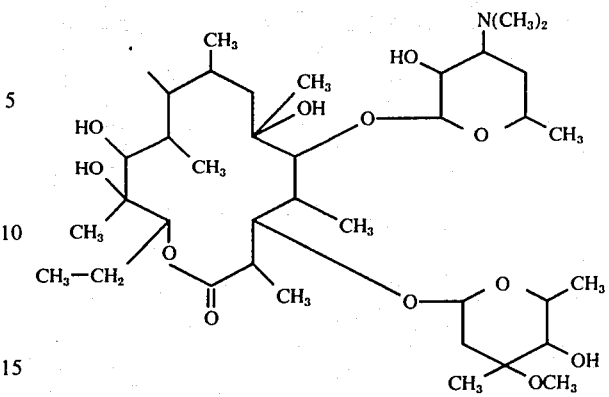

$R_1$ is hydrogen; straight or branched alkyl of 1 to 3 carbon atoms; (alkoxy of 1 to 5 carbon atoms)-(alkyl of 1 to 3 carbon atoms); phenyl; or benzyl;

$R_2$ is hydrogen, hydroxyl, straight or branched alkyl of 1 to 3 carbon atoms; or phenyl;

$R_3$ is hydroxyl;
  alkanoyloxy of 1 to 5 carbon atoms; benzoyloxy; straight or branched alkoxy of 1 to 5 carbon atoms; amino;mono(alkyl of 1 5 carbon atoms)-amino;
  dialkyl-amino, where the sum of carbon atoms in the alkyls is from 2 to 8 inclusive;
  mono(hydroxy-alkyl of 1 to 4 carbon atoms)-amino;
  di(hydroxy-alkyl)-amino, where the sum of carbon atoms in the alkyls is from 2 to 8, inclusive; phenyl(alkyl of 1 to 2 carbon atoms)-amino;
  phenyl-amino, where the phenyl moiety may optionally have one or more halogen, alkyl of 1 to 3 carbon atoms, alkoxy of 1 to 3 carbon atoms or hydroxyl substituents attached thereto;
  (alkanoyl of 1 to 5 carbon atoms)-amino; phenyl(alkanoyl of 1 to 5 carbon atoms)-amino; benzoyl-amino; methoxybenzoyl-amino; halobenzoyl-amino; carboxybenzoyl-amino; p-tolylsulfonamino; -HN-NR$_4$R$_5$, where R$_4$ and R$_5$ are alkyl of 1 to 3 carbon atoms or, together with each other and the nitrogen atom to which they are attached, form a 5- to 6-membered heterocycle optionally comprising an additional oxygen, sulfur or nitrogen hetero-atom in the ring, and said additional nitrogen heteroatom optionally having an alkyl of 1 to 5 carbon atoms substituent attached thereto;

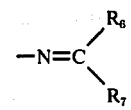

where $R_6$ is amino; mono(straight or branched alkyl of 1 to 8 carbon atoms)-amino; dialkyl-amino, where the sun of carbon atoms in the alkyls is from 2 to 6 inclusive; cyclohexyl-amino; N-(alkyl of 1 to 3 carbon atoms)-N-cyclohexyl-amino; dicyclohexyl- amino; methoxy(alkyl of 1 to 3 carbon atoms)-amino; di-methoxy(alkyl of 1 to 3 carbon atoms)-amino; benzyl-amino, where the phenyl moiety may optionally have from one to three (alkoxy of 1 to 3 carbon atoms)-substituents attached thereto; phenethyl-amino, where the phenyl moiety may optionally have from one to three (alkoxy of 1 to 3 carbon atoms)-substituents attached thereto; dibenzyl-amino; di(phenethyl)-amino; benzhydryl-amino; N-methyl-N-benzyl-amino; N-phenyl- N-benzyl-amino; N-methyl-N-phenyl-amino; N-ethyl-N-phenyl-amino; piperidino; methyl- piperidino; benzyl-piperidino, pyrrol- idino; methyl-pyrrolidino; benzyl-pyrrolidino; morpholino; methyl-morpholino; benzyl-morpholino; piperazino; methyl-piperazino; benzyl-piperazino; hexamethyleneimino; eneimino; methyl-hexamethyleneimino; benzyl-hexamethyleneimino; thiomorpholino; methyl-thiomorpholino; benzyl-thiomorpholino; heptamethyleneimino; methyl-heptamethyleneimino; or benzyl-heptamethylimino; and $R_7$ is amino; cyclohexylamino; di(alkyl of 1 to 3 carbon atoms)-amino; benzyl-amino; phenethyl-amino; dibenzyl-amino; phenoxy-methyl-amino; phenoxyethyl-amino; N-phenyl-N-benzyl-amino; N-methyl-N-phenyl-amino; piperidino, benzyl-piperidino; pyrrolidino; benzyl-pyrrolidino; morpholino; benzyl-morpholino; piperazino; benzyl-piperazino; thiomorpholino; benzyl-thiomorpholino; hexamethyleneimino; benzyl-hexamethyleneimino;

hydrogen; alkyl of 1 to 3 carbon atoms; cyclohexyl, benzyl, methoxy-benzyl; phenethyl; methoxy-phenethyl; thienyl; furyl; pyridyl; (alkyl of 1 to 3 carbon atoms)-thio; methoxy(alkyl of 1 to 3 carbon atoms)-thio; cyano(alkyl of 1 to 3 carbon atoms)-thio; benzyl-thio; methylbenzyl-thio; phenyl-thio; or tolyl-thio;

$R_3 =$ is also-NH-A-B,
where
A is alkylene of 1 to 4 carbon atoms; and
B is alkoxy of 1 to 3 carbon atoms, di(alkyl of 1 to 3 carbon atoms)-amino or carbalkoxy of 2 to 4 carbon atoms;
thiazolyl-amino; or
pyridyl-amino; and
$n$ is 0 or 1;

or a non-toxic, pharmacologically acceptable acid addition salt thereof.

2. A compound of claim 1, which is N-(3-ethylaminopropyl)-erythromycylamine or a pharmacologically acceptable acid addition salt thereof.

3. A compound of claim 1, which is N-[3-(p-chlorobenzylamino-propyl]-erythromycylamine or a pharmacologically acceptable acid addition salt thereof.

4. A compound of claim 1, which is N-(3-[2-hydroxypropylamino]-propyl)-erythromycylamine or a pharmacologically acceptable acid addition salt thereof.

5. A compound of claim 1, which is N-[3-(p-methoxy-benzylamino-propyl]-erythromycyclamine or a pharmacologically acceptable acid addition salt thereof.

6. A compound of claim 1, which is N-[2-morpholinyl-amino)-ethyl]-erythromycylamine or a pharmacologically acceptable acid addition salt thereof.

7. A compound of claim 1, which is N-(2-hydroxyethyl)-erythromycylamine or a pharmacologically acceptable acid addition salt thereof.

8. A compound of claim 1, which is N-{3-[bis-(4-benzylpiperidyl-1)-methyleneamino]-propyl}-erythromyclamine or a pharmacologically acceptable acid addition salt thereof.

9. A compound of claim 1, which is N-{3-[(dibenzylamino)-(4-benzylpiperidyl-1)-methyleneamino]-propyl}-erythromycylamine or a pharmacologically acceptable acid addition salt thereof.

10. A compound of claim 1, which is N-{3-[(furyl-2)-(pyrrolidinyl-1)-methyleneamino]-propyl}-erythromycylamine or a pharmacologically acceptable acid addition salt thereof.

11. A compound of claim 1, which is N-(1-methoxymethyl-2-methoxy-ethyl)-erythromycylamine or a pharmacologically acceptable acid addition salt thereof.

12. An antibacterial pharmaceutical composition consisting essentially of an inert pharmaceutical carrier and an effective antibacterial amount of a compound of claim 1.

13. The method of combatting bacterial infections in a warm-blooded host, which comprises perorally or parenterally administering to said host an effective antibacterial amount of a compound of claim 1.

* * * * *

UNITED STATES PATENT OFFICE
CERTIFICATE OF CORRECTION

Patent No. 4,016,263                     Dated April 5, 1977

Inventor(s) BERND WETZEL, EBERHARD WOITUN, ROLAND MAIER, WOLFGANG REUTER, HANNS GOETH and UWE LECHNER It is certified that error appears in the above-identified patent and that said Letters Patent are hereby corrected as shown below:

Column 1, line 35 - "(akoxy" should read -- alkoxy --

" " " 62 - "p-tolysulfonamino" should read -- p-tolylsulfonamino --

" 2, " 23 - "di(phenyl)" should read -- di(phenethyl) --

" " " 26 - "methy" should read -- methyl --

" " " 39 - "H-phenyl-" should read -- N-phenyl- --

" " " 43 - "benzyl-thiomorpholine" should read -- benzyl-thiomorpholino --

" 3, " 66 - "catlytic" should read -- catalytic --

" 5, " 29 - "-hn-a-b" should read -- -HN-A-B --

" 6, " 31 - "substitured" should read -- substituted --

" " " 50 - "erthromycylamine" should read -- erythromycylamine --

" " " 65 - "substitured" should read -- substituted --

UNITED STATES PATENT OFFICE
CERTIFICATE OF CORRECTION

Patent No. 4,016,263  Dated April 15, 1977

Inventor(s) BERND WETZEL, EBERHARD WOITUN, ROLAND MAIER, WOLFGANG REUTER, HANNS GOETH and UWE LECHNER It is certified that error appears in the above-identified patent and that said Letters Patent are hereby corrected as shown below:

| | | | | |
|---|---|---|---|---|
| Column | 7, | line | 24 | - "quanidino" should read -- guanidino -- |
| " | 9, | " | 14 | - Before "N-" insert -- c. -- |
| " | 12, | " | 9 | - "-S-dioxide" should read -- -S-S-dioxide -- |
| " | 15, | " | 49 | - "erthyromycylamine" should read -- erythromycylamine - |
| " | 17, | " | 56 | - Delete -- with p-chlorobenzaldehyde -- |
| " | 19, | " | 9 | - "N-(2,6-" should read -- N-(2-[2,6- -- |
| " | 20, | " | 1 | - "[(pyrralidino)-" should read -- [(pyrrolidino)- -- |
| " | " | " | 11 | - "erthromycylamine" should read -- erythromycylamine -- |
| " | 21, | " | 17 | - ".p. 132°" should read -- m.p. 132- -- |
| " | " | " | 26 | - "N-{2-" should read -- N-{[2- -- |
| " | 22, | " | 49 | - "dicyclohexylamino" should read -- (dicyclohexylamino) -- |
| " | 23, | " | 6 | - "1H-Hazepine" should read -- 1H-azepine |

UNITED STATES PATENT OFFICE
CERTIFICATE OF CORRECTION

Patent No. 4,016,263          Dated April 15, 1977

Inventor(s) BERND WETZEL, EBERHARD WOITUN, ROLAND MAIER, WOLFGANG REUTER, HANNS GOETH and UWE LECHNER It is certified that error appears in the above-identified patent and that said Letters Patent are hereby corrected as shown below:

| | | | | |
|---|---|---|---|---|
| Column 24, | line | 48 | - | "erythromycylamino" should read -- erythromycylamine -- |
| " | 25, | " | 25 | - "Pyrrolidinyl-" should read -- Pyrrolidinyl-1- -- |
| " | " | " | 42 | - "24°" should read -- 124° -- |
| " | 28, | " | 49 | - "diemthylamino" should read -- dimethylamino -- |
| " | 29, | " | 27 | - "lyl" should read -- 1-yl -- |
| " | " | " | 29 | - "benzylpiperridyl" should read -- benzylpiperidyl -- |
| " | " | " | 31 | - "benzylpiperidyll" should read -- benzylpiperidyl-1 -- |
| " | " | " | 32 | - "erythromcyclamine" should read -- erythromcylamine -- |
| " | " | " | 33 | - "Furyl2" should read -- Furyl-2 -- |
| " | " | " | " | - "pyrrolindinyll" should read -- pyrrolidinyl-1 -- |

UNITED STATES PATENT OFFICE
CERTIFICATE OF CORRECTION

Patent No. 4,016,263      Dated April 15, 1977

Inventor(s) BERND WETZEL, EBERHARD WOLTUN, ROLAND MAIER, WOLFGANG REUTER, HANNS GOETH and UWE LECHNER It is certified that error appears in the above-identified patent and that said Letters Patent are hereby corrected as shown below:

Column 29, line 50 - "[ -(Diethylamino)" should read -- [ 1-(Diethylamino) --

" 30, " 38 - "tearate" should read -- stearate --

" 32, " 26 - "1 5" should read -- of 1 to 5 --

" 33, " 14 - Delete "eneimino"

Signed and Sealed this thirtieth Day of August 1977

[SEAL]

Attest:

RUTH C. MASON
*Attesting Officer*

C. MARSHALL DANN
*Commissioner of Patents and Trademarks*